US012560573B2

(12) United States Patent
Watanabe et al.

(10) Patent No.: US 12,560,573 B2
(45) Date of Patent: Feb. 24, 2026

(54) GAS SENSOR AND CONTROL METHOD OF GAS SENSOR

(71) Applicant: NGK INSULATORS, LTD., Nagoya (JP)

(72) Inventors: Yusuke Watanabe, Nagoya (JP); Daichi Ichikawa, Nagoya (JP); Kodai Ichikawa, Nisshin (JP); Takayuki Sekiya, Nisshin (JP)

(73) Assignee: NGK INSULATORS, LTD., Nagoya (JP)

( * ) Notice: Subject to any disclaimer, the term of this patent is extended or adjusted under 35 U.S.C. 154(b) by 621 days.

(21) Appl. No.: 18/079,035

(22) Filed: Dec. 12, 2022

(65) Prior Publication Data

US 2023/0194462 A1 Jun. 22, 2023

(30) Foreign Application Priority Data

Dec. 17, 2021 (JP) ................................. 2021-205179

(51) Int. Cl.
  *G01N 27/409* (2006.01)
  *G01N 33/00* (2006.01)
(52) U.S. Cl.
  CPC ....... *G01N 27/409* (2013.01); *G01N 33/0027* (2013.01)
(58) Field of Classification Search
  CPC ............. G01N 27/409; G01N 33/0027; G01N 27/417; G01N 27/4175; G01N 27/4071; G01N 27/4074; G01N 27/4075
  See application file for complete search history.

(56) References Cited

U.S. PATENT DOCUMENTS

2005/0230248 A1* 10/2005 Kawase ............. G01N 27/4175
                                                         204/426
2010/0243447 A1 9/2010 Fujisaki et al.
                        (Continued)

FOREIGN PATENT DOCUMENTS

| JP | 5323752 B2 | 10/2013 |
|---|---|---|
| JP | 2021-162580 A | 10/2021 |
| JP | 2021-162581 A | 10/2021 |

OTHER PUBLICATIONS

Kalyakin. Combined amperometric-potentiometric oxygen sensor. Sensors and Actuators B: Chemical 2020. 313, pp. 1-6 (Year: 2020).*

*Primary Examiner* — Luan V Van
*Assistant Examiner* — Randall Lee Gamble, Jr.
(74) *Attorney, Agent, or Firm* — MATTINGLY & MALUR, PC

(57) ABSTRACT

A gas sensor includes a sensor element and a control unit for controlling the sensor element. The sensor element includes: an adjustment pump cell for adjusting an oxygen concentration in a measurement-object gas to a desired concentration; a current measurement pump cell for detecting a target gas to be measured in the measurement-object gas as a current value, the current measurement pump cell including: an inner measurement electrode and an outer measurement electrode; a reference electrode; and an electromotive force detection sensor cell for detecting an electromotive force value between the inner measurement electrode and the reference electrode. The control unit includes a switching unit for switching whether a current flows through the current measurement pump cell or not.

13 Claims, 6 Drawing Sheets

(56) References Cited

U.S. PATENT DOCUMENTS

2020/0003725 A1* 1/2020 Nakagaki ............. G01N 27/417
2021/0302355 A1 9/2021 Sekiya et al.
2021/0302358 A1 9/2021 Sekiya et al.

* cited by examiner

Figure 6:
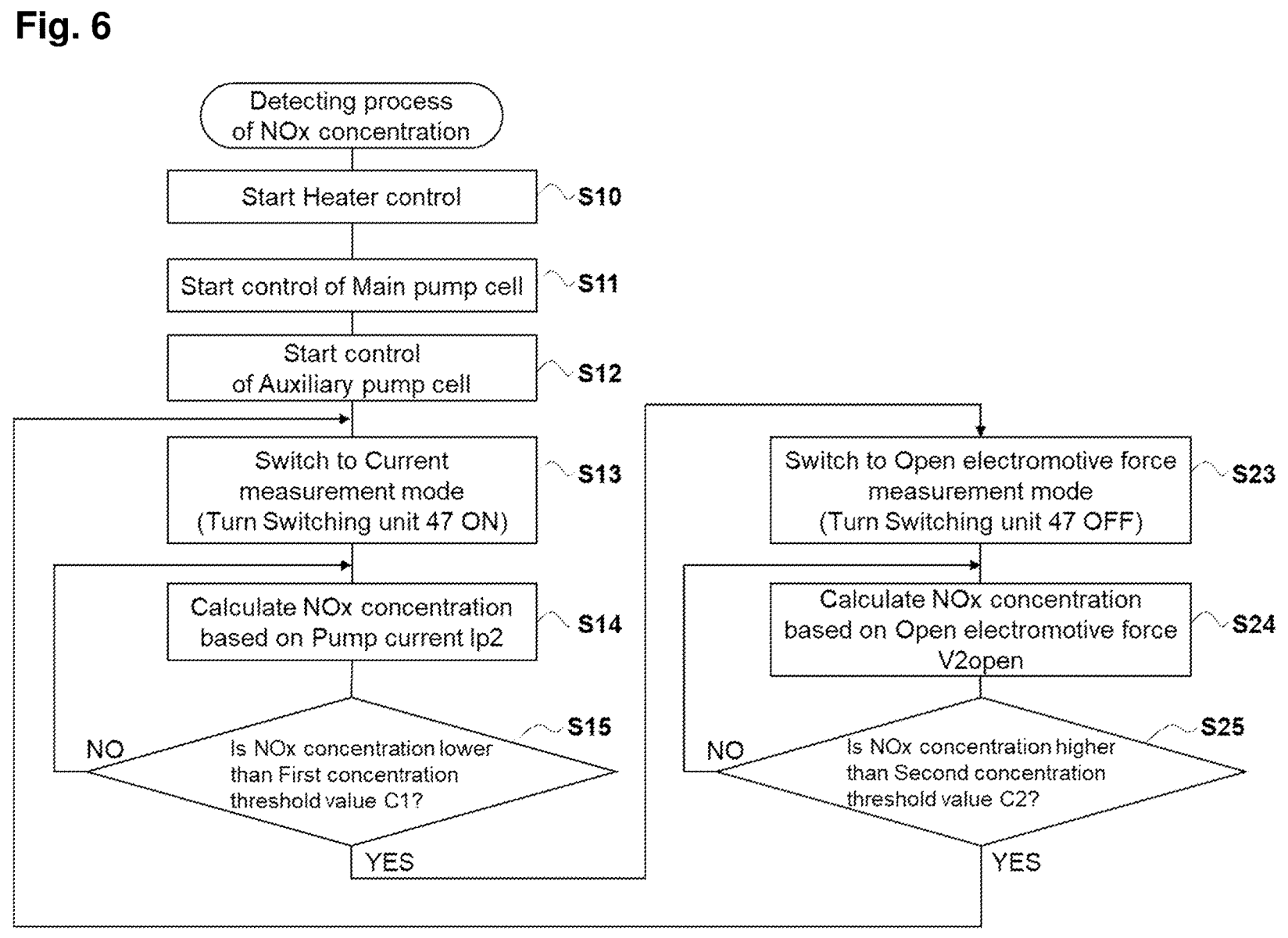

Detecting process of NOx concentration

Start Heater control — S10

Start control of Main pump cell — S11

Start control of Auxiliary pump cell — S12

Switch to Current measurement mode (Turn Switching unit 47 ON) — S13

Calculate NOx concentration based on Pump current Ip2 — S14

Is NOx concentration lower than First concentration threshold value C1? — S15
NO / YES Switch to Open electromotive force measurement mode (Turn Switching unit 47 OFF) — S23

Calculate NOx concentration based on Open electromotive force V2open — S24

Is NOx concentration higher than Second concentration threshold value C2? — S25
NO / YES

GAS SENSOR AND CONTROL METHOD OF GAS SENSOR

CROSS-REFERENCE TO RELATED APPLICATION

The present application claims priority from Japanese application JP2021-205179, filed on Dec. 17, 2021, the contents of which is hereby incorporated by reference into this application.

BACKGROUND OF THE INVENTION

Technical Field of the Invention

The present invention relates to a gas sensor and a control method of the gas sensor.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, conventionally, the concentration of the objective gas component in exhaust gas of an automobile is measured, and an exhaust gas cleaning system mounted on the automobile is optimally controlled based on the measurement.

As such a gas sensor, a gas sensor using an oxygen ion conductive solid electrolyte such as zirconia ($ZrO_2$) is known. For example, JP 5323752 B2 discloses a gas sensor that measures a concentration of an objective gas component in a measurement-object gas by a limiting current method.

JP 5323752 B2 also discloses a NOx sensor that has a main pump cell and an auxiliary pump cell for adjusting an oxygen concentration, and a measurement pump cell including a measurement electrode for detecting NOx. In the NOx sensor, an oxygen partial pressure in a measurement-object gas is controlled to such a low level that does not substantially affect NOx measurement by the main pump cell and the auxiliary pump cell. NOx in the measurement-object gas whose oxygen partial pressure has been controlled is reduced in the measurement electrode, and a resulting oxygen is pumped out by the measurement pump cell to be detected as a current value.

JP 2021-162580 A and JP 2021-162581 A disclose a gas sensor having two measurement pump cells. JP 2021-162580 A and JP 2021-162581 A also disclose that a specific gas concentration is detected in a broad concentration range (for example, 500 ppm or more and 10000 ppm or less) by switching which of the two measurement pump cells is used depending on the specific gas concentration in the measurement-object gas.

CITATION LIST

Patent Documents

Patent Document 1: JP 5323752 B2
Patent Document 2: JP 2021-162580 A
Patent Document 3: JP 2021-162581 A

SUMMARY OF THE INVENTION

Problems to be Solved by the Invention

With the tightening of automobile exhaust emission regulations and the like, a gas sensor is required to accurately measure even a lower-concentration target gas to be measured. Here, the low concentration means a concentration of, for example, about lower than 500 ppm, lower than 400 ppm, lower than 300 ppm, lower than 200 ppm, or lower than 100 ppm.

In a conventional limiting current type gas sensor, for example, as disclosed in JP 5323752 B2, the oxygen generated by reduction of the target gas to be measured (for example, NOx) is detected as a current value in the measurement pump cell. Therefore, the current value is detected as a value corresponding to a concentration of the target gas to be measured.

By the way, even when the target gas to be measured is not present in the measurement-object gas, the current value does not become zero, and a small current flows through the measurement pump cell. This small current is called an offset current. The offset current flows regardless of the concentration of the target gas to be measured. Thus, if the current value of the offset current changes for some factors, a current value detected in the measurement pump cell shifts by the amount of the offset current value change regardless of the concentration of the target gas to be measured. When measuring low concentration of the target gas to be measured, the current value detected in the measuring pump cell in accordance with the concentration of the target gas to be measured is relatively small, so the change in the current value due to the offset current value change is relatively large, and the effect on measurement accuracy tends to be large.

It is therefore an object of the present invention to accurately measure even a low-concentration target gas to be measured. Specifically, it is an object of the present invention to accurately measure a target gas to be measured in a wide concentration range including a low-concentration target gas to be measured.

Means for Solving the Problems

As a result of intensive studies, the present inventors have found that, by equipping a gas sensor with a switching unit for switching whether a current flows through a current measurement pump cell or not, it is possible to eliminate the effect of the offset current and accurately measure a low concentration of a target gas to be measured.

The present invention includes the following aspects.

(1) A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow part formed from one end part in a longitudinal direction of the base part;

an adjustment pump cell for adjusting an oxygen concentration in a measurement-object gas to a desired concentration, the adjustment pump cell including: an inner pump electrode disposed on an inner surface of the measurement-object gas flow part; and an outer pump electrode disposed at a position different from the measurement-object gas flow part on the base part and corresponding to the inner pump electrode;

a current measurement pump cell for detecting a target gas to be measured in the measurement-object gas as a current value, the current measurement pump cell including: an inner measurement electrode disposed at a position farther from the one end part in the longitudinal direction of the base part than the inner pump electrode on the inner surface of the measurement-object gas flow part; and an outer measurement electrode disposed at a position different from the measurement-object gas flow part on the base part and corresponding to the inner measurement electrode;

a reference electrode disposed inside the base part to be in contact with a reference gas; and an electromotive force detection sensor cell for detecting an electromotive force value between the inner measurement electrode and the reference electrode, the electromotive force detection sensor cell including the inner measurement electrode and the reference electrode, and the control unit comprises:

a switching unit for switching whether a current flows through the current measurement pump cell or not.

In the electromotive force detection sensor cell, the reference electrode corresponds to the inner measurement electrode.

(2) The gas sensor according to the above (1), wherein the control unit comprises:

a measurement mode switching part for switching between an electromotive force measurement mode in which a concentration of the target gas to be measured in the measurement-object gas is detected based on an electromotive force value in the electromotive force detection sensor cell, and a current measurement mode in which a concentration of the target gas to be measured in the measurement-object gas is detected based on a current value in the current measurement pump cell, and the measurement mode switching part switches the switching unit so that a current does not flow through the current measurement pump cell in case of switching to the electromotive force measurement mode, and switches the switching unit so that a current flows through the current measurement pump cell in case of switching to the current measurement mode.

(3) The gas sensor according to the above (1) or (2), wherein the switching unit comprises a switch for switching whether a conduction in the current measurement pump cell is cut off or not.

(4) The gas sensor according to the above (3), wherein the measurement mode switching part turns off the switch to cut off a conduction in the current measurement pump cell so that a current does not flow through the current measurement pump cell in case of switching to the electromotive force measurement mode, and turns on the switch to conduct the current measurement pump cell so that a current flows through the current measurement pump cell in case of switching to the current measurement mode.

(5) The gas sensor according to the above (1) or (2), wherein the switching unit comprises a variable power supply for changing a voltage applied to the current measurement pump cell.

(6) The gas sensor according to the above (5), wherein the measurement mode switching part sets a voltage in the variable power supply to zero not to apply a voltage in the current measurement pump cell so that a current does not flow through the current measurement pump cell in case of switching to the electromotive force measurement mode, and sets a voltage in the variable power supply to a predetermined value to apply the predetermined voltage in the current measurement pump cell so that a current flows through the current measurement pump cell in case of switching to the current measurement mode.

(7) The gas sensor according to any one of the above (2) to (6), wherein the measurement mode switching part switches to the electromotive force measurement mode when the measurement mode switching part determines that a concentration of the target gas to be measured detected in the current measurement mode is lower than a predetermined first concentration threshold value $C1$, and the measurement mode switching part switches to the current measurement mode when the measurement mode switching part determines that a concentration of the target gas to be measured detected in the electromotive force measurement mode is higher than a predetermined second concentration threshold value $C2$.

That is, in a low concentration range where the concentration of the target gas to be measured in the measurement-object gas is lower than the first concentration threshold value $C1$, a concentration of the target gas to be measured is detected in the electromotive force measurement mode with higher measurement accuracy in the low concentration range; and in a high concentration range where the concentration of the target gas to be measured in the measurement-object gas is higher than the second concentration threshold value $C2$, a concentration of the target gas to be measured is detected in the current measurement mode with higher measurement accuracy in the high concentration range.

(8) The gas sensor according to the above (7), wherein the first concentration threshold value $C1$ is lower than the second concentration threshold value $C2$.

(9) The gas sensor according to any one of the above (2) to (8), wherein in the current measurement mode, a current value in the current measurement pump cell is controlled so that an electromotive force value between the inner measurement electrode and the reference electrode in the electromotive force detection sensor cell is a predetermined value.

(10) The gas sensor according to any one of the above (1) to (8), wherein the reference electrode functions as the outer measurement electrode.

(11) A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow part formed from one end part in a longitudinal direction of the base part;

an adjustment pump cell for adjusting an oxygen concentration in a measurement-object gas to a desired concentration, the adjustment pump cell including: an inner pump electrode disposed on an inner surface of the measurement-object gas flow part; and an outer pump electrode disposed at a position different from the measurement-object gas flow part on the base part and corresponding to the inner pump electrode;

a current measurement pump cell for detecting a target gas to be measured in the measurement-object gas as a current value, the current measurement pump cell including: an inner measurement electrode disposed at a position farther from the one end part in the longitudinal direction of the base part than the inner pump electrode on the inner surface of the measurement-object gas flow part; and an outer measurement electrode disposed at a position different from the measurement-object gas flow part on the base part and corresponding to the inner measurement electrode;

a reference electrode disposed inside the base part to be in contact with a reference gas; and an electromotive force detection sensor cell for detecting an electromotive force value between the inner measurement electrode and the reference electrode, the electromotive force detection sensor cell including the inner measurement electrode and the reference electrode, and the control unit comprises:

a switching unit for switching whether a current flows through the current measurement pump cell or not, and the control method comprising:

a concentration detecting step of performing an electromotive force measurement mode in which the adjustment pump cell is operated and the current measurement pump cell is not operated to detect a concentration of the target gas to be measured in the measurement-object gas based on an electromotive force value in the electromotive force detection sensor cell, or a current measurement mode in which the adjustment pump cell and the current measurement pump cell are operated to detect a concentration of the target gas to be measured in the measurement-object gas based on a current value in the current measurement pump cell, while switching between the electromotive force measurement mode and the current measurement mode by using the switching unit.

(12) The control method according to the above (11), wherein, in the concentration detecting step, the switching unit is switched so that a current does not flow through the current measurement pump cell to switch to the electromotive force measurement mode when a concentration of the target gas to be measured detected in the current measurement mode is determined to be lower than a predetermined first concentration threshold value C1, and the switching unit is switched so that a current flows through the current measurement pump cell to switch to the current measurement mode when a concentration of the target gas to be measured detected in the electromotive force measurement mode is determined to be higher than a predetermined second concentration threshold value C2.

(13) The control method according to the above (12), wherein the first concentration threshold value C1 is lower than the second concentration threshold value C2.

Advantageous Effect of the Invention

According to the present invention, it is possible to accurately measure even a low-concentration target gas to be measured. Specifically, according to the present invention, it is possible to accurately measure a target gas to be measured in a wide concentration range including a low-concentration target gas to be measured.

6

BRIEF DESCRIPTION OF THE DRAWINGS

FIG. 1 is a vertical sectional schematic view in a longitudinal direction, showing one example of a general configuration of a gas sensor 100.

FIG. 6 is a flow chart showing one example of detecting process of NOx concentration in the gas sensor 100.

MODES FOR CARRYING OUT OF THE INVENTION

A gas sensor of the present invention includes a sensor element and a control unit for controlling the sensor element.

The sensor element contained in the gas sensor of the present invention includes:

a base part in an elongated plate shape, including an oxygen-ion-conductive solid electrolyte layer;

a measurement-object gas flow part formed from one end part in a longitudinal direction of the base part;

an adjustment pump cell for adjusting an oxygen concentration in a measurement-object gas to a desired concentration, the adjustment pump cell including: an inner pump electrode disposed on an inner surface of the measurement-object gas flow part; and an outer pump electrode disposed at a position different from the measurement-object gas flow part on the base part and corresponding to the inner pump electrode;

a current measurement pump cell for detecting a target gas to be measured in the measurement-object gas as a current value, the current measurement pump cell including: an inner measurement electrode disposed at a position farther from the one end part in the longitudinal direction of the base part than the inner pump electrode on the inner surface of the measurement-object gas flow part; and an outer measurement electrode disposed at a position different from the measurement-object gas flow part on the base part and corresponding to the inner measurement electrode;

a reference electrode disposed inside the base part to be in contact with a reference gas; and an electromotive force detection sensor cell for detecting an electromotive force value between the inner measurement electrode and the reference electrode, the electromotive force detection sensor cell including the inner measurement electrode and the reference electrode. Here, in the electromotive force detection sensor cell, the reference electrode corresponds to the inner measurement electrode.

The control unit contained in the gas sensor of the present invention includes a switching unit for switching whether a current flows through the current measurement pump cell or not.

Hereinafter, an example of an embodiment of a gas sensor of the present invention will be described in detail.

[General Configuration of Gas Sensor]

Figure 1:
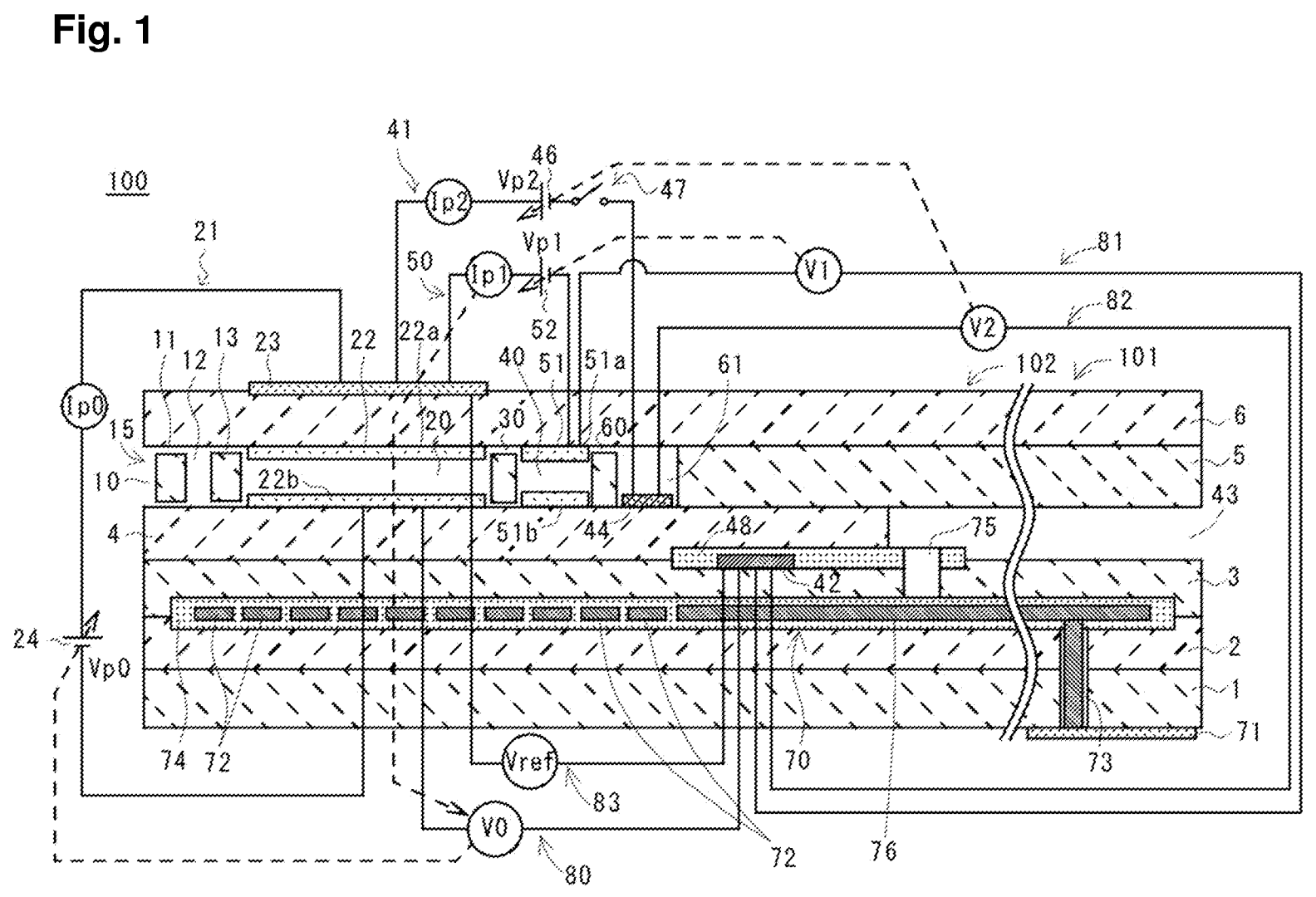

The gas sensor of the present invention will now be described with reference to the drawings. FIG. 1 is a vertical sectional schematic view in the longitudinal direction, showing one example of a general configuration of a gas sensor 100 including a sensor element 101. Hereinafter, based on FIG. 1, the upper side and the lower side in FIG. 1 are respectively defined as top and bottom, and the left side and the right side in FIG. 1 are respectively defined as a front end side and a rear end side.

In FIG. 1, the gas sensor 100 represents one example of a NOx sensor that detects NOx in a measurement-object gas by the sensor element 101, and measures the concentration of NOx.

Figure 2:
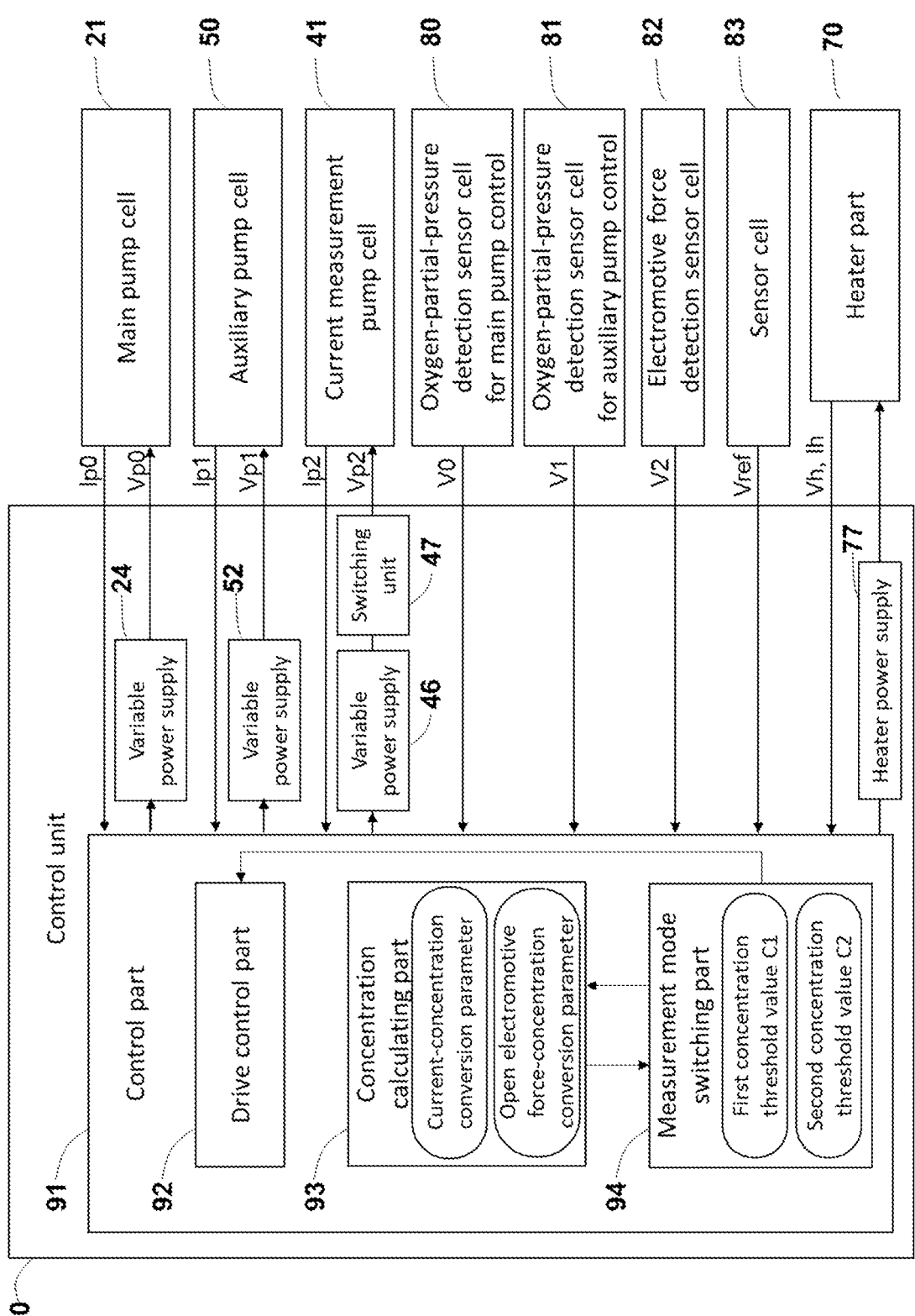
FIG. 2 is a block diagram showing electric connections between a control unit 90 and respective pump cells 21, 50, and 41, respective sensor cells 80, 81, 82, and 83, and heater part 70 of a sensor element 101.

Further, the gas sensor 100 includes a control unit 90 for controlling the sensor element 101. The control unit 90 includes a switching unit 47 for switching whether a current flows through the current measurement pump cell or not. FIG. 2 is a block diagram showing electric connections between the control unit 90 and the sensor element 101.

In the gas sensor 100, the switching unit 47 may have a mechanism for switching whether a current flows through a current measurement pump cell 41 or not. For example, the switching unit 47 may be a switch 47 as illustrated in FIG. 1, or a mechanism including a switch. The switch may be a contact switch that mechanically opens and closes a contact on an electrical circuit, or may be a switch using a switching element that turn on and off the current flowing in the electrical circuit. The switching element includes a diode, a thyristor, a transistor, a MOSFET, and the like. The configuration of the switch may appropriately be determined by a person skilled in the art. By turning the switch OFF, it is possible to cut off a conduction in the current measurement pump cell 41 to switch so that a current does not flow through the current measurement pump cell 41. By turning the switch ON, it is possible to conduct the current measurement pump cell 41 to switch so that a current flows through the current measurement pump cell 41.

Alternatively, for example, the switching unit 47 may be a variable power supply 46, or a mechanism including the variable power supply 46. By setting a voltage in the variable power supply 46 to zero, it is possible to not to apply a voltage in the current measurement pump cell to switch so that a current does not flow through the current measurement pump cell. By setting a voltage in the variable power supply 46 to a predetermined value, it is possible to apply the voltage in the current measurement pump cell to switch so that a current flows through the current measurement pump cell.

(Sensor Element)

The sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$) The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 1, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow part 15 is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute internal spaces of the sensor element 101. Each of the internal spaces is provided in such a manner that a portion of the spacer layer 5 is hollowed out, and the top of each of the internal spaces is defined by the lower surface of the second solid electrolyte layer 6, the bottom of each of the internal spaces is defined by the upper surface of the first solid electrolyte layer 4, and the lateral surface of each of the internal spaces is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 1). Each of the first diffusion-rate limiting part 11, and the second diffusion-rate limiting part 13 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 1) between the spacer layer 5 and the second solid electrolyte layer 6. The fourth diffusion-rate limiting part 60 may be in such a form that a desired diffusion resistance is created, but the form is not limited to the slit.

Also, at a position farther from the front end than the measurement-object gas flow part 15, a reference gas introduction space 43 is disposed between the upper surface of the third substrate layer 3 and the lower surface of the spacer layer 5 at a position where the reference gas introduction space 43 is laterally defined by the lateral surface of the first solid electrolyte layer 4. The reference gas introduction space 43 has an opening in the other end part (hereinafter, referred to as a rear end part) of the sensor element 101. As a reference gas for NOx concentration measurement, for example, air is introduced into the reference gas introduction space 43.

An air introduction layer 48 is a layer formed of porous alumina, and is so configured that a reference gas is introduced into the air introduction layer 48 via the reference gas introduction space 43. The air introduction layer 48 is formed to cover a reference electrode 42.

The reference electrode 42 is an electrode sandwiched between the upper surface of the third substrate layer 3 and the first solid electrolyte layer 4, and as described above, the air introduction layer 48 leading to the reference gas introduction space 43 is disposed around the reference electrode 42. That is, the reference electrode 42 is disposed to be in contact with a reference gas via the air introduction layer 48 which is a porous material, and the reference gas introduction space 43. As will be described later, the reference electrode 42 can be used to measure the oxygen concentration (oxygen partial pressure) in the first internal cavity 20, the second internal cavity 40, and the third internal cavity 61. The reference electrode 42 is formed as a porous cermet electrode (e.g., a cermet electrode of Pt and $ZrO_2$).

In the measurement-object gas flow part 15, the gas inlet 10 is open to the external space, and the measurement-object gas is taken into the sensor element 101 from the external space through the gas inlet 10.

In the present embodiment, the measurement-object gas flow part 15 is in such a form that the measurement-object gas is introduced through the gas inlet 10 that is open on the front end surface of the sensor element 101, however, the present invention is not limited to this form. For example, the measurement-object gas flow part 15 need not have a recess of the gas inlet 10. In this case, the first diffusion-rate limiting part 11 substantially serves as a gas inlet.

For example, the measurement-object gas flow part 15 may have an opening that communicates with the buffer space 12 or a position near the buffer space 12 of the first internal cavity 20, on a lateral surface along the longitudinal direction of the base part 102. In this case, the measurement-object gas is introduced from the lateral surface along the longitudinal direction of the base part 102 through the opening.

Further, for example, the measurement-object gas flow part 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The sensor element 101 includes an adjustment pump cell that includes an inner pump electrode disposed on an inner surface of the measurement-object gas flow part 15, and an outer pump electrode disposed at a position different from the measurement-object gas flow part 15 on the base part 102 and corresponding to the inner pump electrode. In this embodiment, the main pump cell 21 and an auxiliary pump cell 50 function as the adjustment pump cells. Further, an inner main pump electrode 22 and an auxiliary pump electrode 51 function as the inner pump electrodes, and an outer pump electrode 23 functions as the outer pump electrode.

The main pump cell 21 is an electrochemical pump cell including the inner main pump electrode 22 disposed on an inner surface of the measurement-object gas flow part 15, and the outer pump electrode 23 disposed at a position different from the measurement-object gas flow part 15 on the base part 102 (in FIG. 1, on an outer surface of the base part 102) and corresponding to the inner main pump electrode 22. The phrase "corresponding to the inner main pump electrode 22" means that the outer pump electrode 23 and the inner main pump electrode 22 are provided with the second solid electrolyte layer 6 being interposed therebetween.

That is, the main pump cell 21 is an electrochemical pump cell composed of the inner main pump electrode 22 having a ceiling electrode portion 22a disposed over substantially the entire surface of the lower surface of the second solid electrolyte layer 6 that faces the first internal cavity 20, the outer pump electrode 23 disposed on a region of the upper surface of the second solid electrolyte layer 6 that corresponds to the ceiling electrode portion 22a so as to be exposed to the external space, and the second solid electrolyte layer 6 sandwiched between the inner main pump electrode 22 and the outer pump electrode 23.

The inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22a is formed on the lower surface of the second solid electrolyte layer 6 that defines the ceiling surface of the first internal cavity 20, and a bottom electrode portion 22b is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22*a* and the bottom electrode portion 22*b*. Thus, the inner main pump electrode 22 is provided as a tunnel-like structure in the area where the lateral electrode portions are disposed.

The inner main pump electrode 22 and the outer pump electrode 23 are porous cermet electrodes (electrodes in a state that a metal component and a ceramic component are mixed). The ceramic component to be used is not particularly limited, but is preferably an oxygen-ion-conductive solid electrolyte as in the case of the base part 102. For example, $ZrO_2$ can be used as the ceramic component.

The inner main pump electrode 22 to be in contact with a measurement-object gas is formed using a material having a weakened reducing ability with respect to a NOx component in the measurement-object gas. The inner main pump electrode 22 preferably contains a noble metal having catalytic activity (e.g., at least one of Pt, Rh, Ir, Ru, and Pd) and a noble metal (e.g., Au, Ag) that reduces the catalytic activity of a noble metal having catalytic activity with respect to a target gas to be measured (in this embodiment, NOx). In this embodiment, the inner main pump electrode 22 is formed as a porous cermet electrode made of Pt containing 1% of Au and $ZrO_2$.

The outer pump electrode 23 may contain the above-described noble metal having catalytic activity. Similarly, the reference electrode 42 may contain the above-described noble metal having catalytic activity. In this embodiment, the outer pump electrode 23 is formed as a porous cermet electrode made of Pt and $ZrO_2$.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force V0 measured in the oxygen-partial-pressure detection sensor cell 80 for main pump control. In addition, the pump current Ip0 is controlled by performing feedback control of the pump voltage Vp0 in the variable power supply 24 so that the electromotive force V0 is constant. Thus, the oxygen concentration in the first internal cavity 20 can be maintained at a predetermined constant value.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21, and guides the measurement-object gas into the second internal cavity 40.

The second internal cavity 40 is provided as a space for adjusting the oxygen partial pressure in the measurement-object gas introduced through the third diffusion-rate limiting part 30 more accurately. The oxygen partial pressure is adjusted by operation of the auxiliary pump cell 50. The sensor element 101 may be configured without the second internal cavity 40 and the auxiliary pump cell 50. From the viewpoint of adjusting accuracy of oxygen partial pressure, it is more preferred that the second internal cavity 40 and the auxiliary pump cell 50 be provided.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an electrochemical pump cell including the auxiliary pump electrode 51 disposed at a position farther from the front end portion in the longitudinal direction of the base part 102 than the inner main pump electrode 22 on the inner surface of the measurement-object gas flow part 15, and the outer pump electrode 23 disposed at a position different from the measurement-object gas flow part 15 on the base part 102 (in FIG. 1, on the outer surface of the base part 102) and corresponding to the auxiliary pump electrode 51. The phrase "corresponding to the auxiliary pump electrode 51" means that the outer pump electrode 23 and the auxiliary pump electrode 51 are provided with the second solid electrolyte layer 6 being interposed therebetween.

That is, the auxiliary pump cell 50 is an auxiliary electrochemical pump cell composed of the auxiliary pump electrode 51 having a ceiling electrode portion 51*a* disposed on substantially the entire surface of lower surface of the second solid electrolyte layer 6 facing with the second internal cavity 40, the outer pump electrode 23 (the outer electrode is not limited to the outer pump electrode 23, but may be any suitable electrode outside the sensor element 101), and the second solid electrolyte layer 6.

This auxiliary pump electrode 51 is disposed in the second internal cavity 40 in a tunnel-like structure similar to the inner main pump electrode 22 disposed in the first internal cavity 20 described previously. Specifically, in the tunnel-like structure, the ceiling electrode portion 51*a* is formed on the second solid electrolyte layer 6 that defines the ceiling surface of the second internal cavity 40, a bottom electrode portion 51*b* is formed on the first solid electrolyte layer 4 that defines the bottom surface of the second internal cavity 40, and lateral electrode portions (not shown) connecting the ceiling electrode portion 51*a* and the bottom electrode portion 51*b* are formed on the wall surfaces of the spacer layer 5 that define the lateral walls of the second internal cavity 40.

It is to be noted that the auxiliary pump electrode 51 is formed using a material having a weakened ability to reduce a NOx component in the measurement-object gas, as with the case of the inner main pump electrode 22. The auxiliary pump electrode 51, as with the case of the inner main pump electrode 22, preferably contains a noble metal having catalytic activity (e.g., at least one of Pt, Rh, Ir, Ru, and Pd) and a noble metal (e.g., Au, Ag) that reduces the catalytic activity of a noble metal having catalytic activity with respect to a target gas to be measured (in this embodiment, NOx). In this embodiment, the auxiliary pump electrode 51 is formed as a porous cermet electrode made of Pt containing 1% of Au and $ZrO_2$.

In the auxiliary pump cell 50, by applying a desired voltage Vp1 between the auxiliary pump electrode 51 and the outer pump electrode 23 by a variable power supply 52, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with the variable power supply 52 whose voltage is controlled on the basis of an electromotive force V1 detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 is used for control of the electromotive force V0 of the oxygen-partial-pressure detection sensor cell 80 for main pump control. Specifically, the pump current Ip1 is input to the oxygen-partial-pressure detection sensor cell 80 for main pump control as a control signal to control the electromotive force V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. NOx concentration is measured by an electromotive force detection sensor cell 82, or by the operation of the current measurement pump cell 41.

The current measurement pump cell 41 is an electrochemical pump cell including an inner measurement electrode (in this embodiment, a measurement electrode 44) disposed at a position farther from the front end portion in the longitudinal direction of the base part 102 than the inner pump electrode (in this embodiment, the inner main pump electrode 22 and the auxiliary pump electrode 51) on the inner surface of the measurement-object gas flow part 15, and an outer measurement electrode disposed at a position different from the measurement-object gas flow part 15 on the base part 102 and corresponding to the inner measurement electrode. In this embodiment, the outer pump electrode 23 disposed on the outer surface of the base part 102 functions also as the outer measurement electrode. The phrase "corresponding to the inner measurement electrode" means that the outer pump electrode 23 and the measurement electrode 44 are provided with the second solid electrolyte layer 6, the spacer layer 5, and the first solid electrolyte layer 4 being interposed therebetween.

That is, the current measurement pump cell 41 measures NOx concentration in the measurement-object gas in the third internal cavity 61. The current measurement pump cell 41 is an electrochemical pump cell composed of the measurement electrode 44 disposed on the upper surface of the first solid electrolyte layer 4 facing with the third internal cavity 61, the outer pump electrode 23, the second solid electrolyte layer 6, the spacer layer 5, and the first solid electrolyte layer 4.

The measurement electrode 44 is a porous cermet electrode. The measurement electrode 44 functions also as a NOx reduction catalyst that reduces NOx present in the atmosphere in the third internal cavity 61. The measurement electrode 44 is an electrode containing a noble metal having catalytic activity (e.g., at least one of Pt, Rh, Jr, Ru, and Pd). It is preferred that the measurement electrode 44 does not contain a noble metal (e.g., Au, Ag) that reduces the catalytic activity of a noble metal having catalytic activity with respect to a target gas to be measured (in this embodiment, NOx). In this embodiment, the measurement electrode 44 is formed as a porous cermet electrode made of Pt and Rh, and $ZrO_2$.

The electromotive force detection sensor cell 82 includes the inner measurement electrode (in this embodiment, the measurement electrode 44) and the reference electrode 42, and is configured to detect an electromotive force value between the inner measurement electrode and the reference electrode 42. Here, the reference electrode 42 corresponds to the measurement electrode 44. The phrase "corresponding to the measurement electrode 44" means that the reference electrode 42 and the measurement electrode 44 are provided with the first solid electrolyte layer 4, and the third substrate layer 3 being interposed therebetween.

That is, the electromotive force detection sensor cell 82 is an electrochemical sensor cell composed of the measurement electrode 44, the first solid electrolyte layer 4, the third substrate layer 3, and the reference electrode 42. The electromotive force detection sensor cell 82 detects the oxygen partial pressure around the measurement electrode 44.

The current measurement pump cell 41 is configured to switch whether a current flows through the current measurement pump cell 41 or not by the switching unit 47. Hereinafter, the gas sensor 100 in which the switching unit 47 is the switch 47 is described as an example with reference to FIG. 1. The switching unit 47 is schematically illustrated in FIG. 1 using a circuit symbol of a contact switch, but the switching unit 47 may be a switch using a switching element. A location of the switching unit 47 is not limited to the position illustrated in FIG. 1, but the switching unit 47 can be located anywhere on the circuit of the current measurement pump cell 41.

When the switching unit 47 is turned OFF, electrical connection of the current measurement pump cell 41 is cut off so that a current does not flow through the current measurement pump cell 41. The phrase "a current does not flow" means that a current value in the current measurement pump cell 41 is zero or substantially zero.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2+O_2$) to generate oxygen. The generated oxygen remains around the measurement electrode 44. As a result, in the electromotive force detection sensor cell 82, an electromotive force is generated corresponding to the difference between the amount of oxygen generated by the reduction of the NOx component in the atmosphere around the measurement electrode 44 and the amount of oxygen contained in the reference air. The generated electromotive force is referred to as an open electromotive force V2open. Since the amount of oxygen contained in the reference air is constant, a value of the open electromotive force V2open is a value corresponding to a concentration of nitrogen oxide in the measurement-object gas. Therefore, nitrogen oxide concentration in the measurement-object gas can be calculated by using the open electromotive force V2open detected in the electromotive force detection sensor cell 82.

When the switching unit 47 is turned ON, the current measurement pump cell 41 is electrically connected so that a current flows through the current measurement pump cell 41.

Also, in this case, the measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced (2NO $N_2+O_2$) to generate oxygen. The generated oxygen is to be pumped by the current measurement pump cell 41. At this time, the electromotive force detected in the electromotive force detection sensor cell 82 is used for a control voltage V2, and a voltage Vp2 of the variable power supply 46 is feedback controlled so that the control voltage V2 is constant. Since the amount of oxygen generated around the measurement electrode 44 is proportional to the concentration of nitrogen oxide in the measurement-object gas, nitrogen oxide concentration in the measurement-object gas can be calculated by using a pump current Ip2 in the current measurement pump cell 41.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force Vref obtained by the sensor cell 83.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater electrode 71, a heater 72, a heater lead 76, a through hole 73, a heater insulating layer 74, and a pressure relief vent 75.

The heater electrode 71 is an electrode formed in contact with the lower surface of the first substrate layer 1. The power can be supplied to the heater part 70 from the outside by connecting the heater electrode 71 with a heater power supply 77 that is an external power supply.

The heater 72 is an electrical resistor sandwiched by the second substrate layer 2 and the third substrate layer 3 from top and bottom. The heater 72 is connected with the heater electrode 71 via a heater lead 76 that connects with the heater 72 and extends in the rear end side in the longitudinal direction of the sensor element 101, and the through hole 73. The heater 72 is externally powered through the heater electrode 71 to generate heat, and heats and maintains the temperature of the solid electrolyte forming the sensor element 101.

The heater 72 is embedded over the whole area from the first internal cavity 20 to the third internal cavity 61 so that the temperature of the entire sensor element 101 can be adjusted to such a temperature that activates the solid electrolyte. The temperature may be adjusted so that the main pump cell 21, the auxiliary pump cell 50, and the current measurement pump cell 41 are operable. It is not necessary that the whole area is adjusted to the same temperature, but the sensor element 101 may have temperature distribution.

In the sensor element 101 of the present embodiment, the heater 72 is embedded in the base part 102, but this form is not limitative. The heater 72 may be disposed to heat the base part 102. That is, the heater 72 may beat the sensor element 101 to develop oxygen ion conductivity with which the main pump cell 21, the auxiliary pump cell 50, and the current measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102.

The heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

The pressure relief vent 75 extends through the third substrate layer 3 so that the heater insulating layer 74 and the reference gas introduction space 43 communicate with each other. The pressure relief vent 75 can mitigate an increase in internal pressure due to temperature rise in the heater insulating layer 74. The pressure relief vent 75 may be absent.

The above-described sensor element 101 is incorporated into the gas sensor 100 in such a form that the front end part of the sensor element 101 comes into contact with the measurement-object gas, and the rear end part of the sensor element 101 comes into contact with the reference gas.

(Control Unit)

The gas sensor 100 of this embodiment includes the sensor element 101 described above and the control unit 90 for controlling the sensor element 101. In the gas sensor 100, each of the electrodes 22, 23, 51, 44, and 42 of the sensor element 101 is electrically connected to the control unit 90 through a lead wire not shown. FIG. 2 is a block diagram showing electric connections between the control unit 90 and the respective pump cells 21, 50, and 41, the respective sensor cells 80, 81, 82, and 83, and the heater part 70 of the sensor element 101. The control unit 90 includes the above-described variable power supplies 24, 46, and 52, the switching unit 47 for switching whether a current flows through the current measurement pump cell 41 or not, and a control part 91. The control part 91 includes a drive control part 92, a concentration calculating part 93, and a measurement mode switching part 94. The switching unit 47 is a component that receives a control signal from the measurement mode switching part 94 and switches whether or not to apply current to the current measurement pump cell 41.

The control part 91 is realized by a general-purpose or dedicated computer, and functions as the drive control part 92, the concentration calculating part 93, and the measurement mode switching part 94 are realized by a CPU, a memory or the like installed in the computer. It is to be noted that when NOx contained in exhaust gas from the engine of a car is a target gas to be measured by the gas sensor 100 and the sensor element 101 is attached to an exhaust gas path, some or all of the functions of the control unit 90 (especially, the control unit 91) may be realized by an electronic control unit (ECU) installed in the car.

The control part 91 is configured to acquire an electromotive force (V0, V1, V2, Vref) in each of the sensor cells 80, 81, 82, and 83, a pump current (Ip0, Ip1, Ip2) in each of the pump cells 21, 50, and 41, and a heater voltage Vh and a heater current Ih in the heater part 70 of the sensor element 101. Further, the control part 91 is configured to output control signals to the variable power supplies 24, 52 and 46, the switching unit 47 and the heater power supply 77.

The drive control part 92 is configured to control the heater part 70, the main pump cell 21, the auxiliary pump cell 50 and the current measurement pump cell 41 so that the gas sensor 100 can measure a concentration of a target gas to be measured (in this embodiment, a NOx).

The drive control part 92 heats the heater 72, and maintains the temperature of the heater 72 at a desired temperature.

In order to heat the heater 72, known various control methods can be used. For example, the heater 72 may be heated by applying a certain voltage to the heater 72. The output of the heater power supply 77 may be controlled on the basis of the resistance value of the heater 72. Alternatively, the output of the heater power supply 77 may be controlled on the basis of at least one of resistance values in the main pump cell 21, the auxiliary pump cell 50, and the current measurement pump cell 41.

For example, the drive control part 92 performs feedback control of a control signal output to the heater power supply 77 on the basis of a heater resistance value Rh ($=$Vh/Ih) calculated from the heater voltage Vh and the heater current Ih in the heater 72 so that the heater 72 reaches a target temperature.

The drive control part 92 performs feedback control of the pump voltage Vp0 of the variable power supply 24 in the main pump cell 21 so that the electromotive force V0 in the oxygen-partial-pressure detection sensor cell 80 for main pump control is at a constant value (referred to as a set value $V0_{SET}$). The electromotive force V0 indicates the oxygen partial pressure in the vicinity of the inner main pump electrode 22, and therefore making the electromotive force V0 constant means that the oxygen partial pressure in the vicinity of the inner main pump electrode 22 is made constant. As a result, the pump current Ip0 in the main pump cell 21 varies depending on the oxygen concentration in the measurement-object gas.

When the oxygen partial pressure in the measurement-object gas is higher than the oxygen partial pressure corresponding to the set value $V0_{SET}$, the main pump cell 21 pumps oxygen out from the first internal cavity 20. On the other hand, when the oxygen partial pressure in the measurement-object gas is lower than the oxygen partial pressure corresponding to the set value $V0_{SET}$ (for example, when hydrocarbons HC or the like are contained), the main pump cell 21 pumps oxygen into the first internal cavity 20 from the space outside the sensor element 101. Therefore, the value of the pump current Ip0 may be either positive or negative.

The drive control part 92 performs feedback control of the pump voltage Vp1 of the variable power supply 52 in the auxiliary pump cell 50 so that the electromotive force V1 in the oxygen-partial-pressure detection sensor cell 81 for auxiliary pump control is at a constant value (referred to as a set value $V1_{SET}$). The electromotive force V1 indicates the oxygen partial pressure in the vicinity of the auxiliary pump electrode 51, and therefore making the electromotive force V1 constant means that the oxygen partial pressure in the vicinity of the auxiliary pump electrode 51 is made constant. The oxygen partial pressure in the atmosphere in the second internal space 40 is thereby controlled to be a low partial pressure that does not substantially affect measurement of NOx.

At the same time, feedback control is performed to set the set value $V0_{SET}$ of the electromotive force V0 on the basis of the pump current Ip1 in the auxiliary pump cell 50 so that the pump current Ip1 is at a constant value (referred to as a set value $Ip1_{SET}$). Specifically, the pump current Ip1 is input, as a control signal, to the oxygen-partial-pressure detection sensor cell 80 for main pump control, and the electromotive force V0 therein is controlled to be the set value $V0_{SET}$ set on the basis of the pump current Ip1 so that the oxygen partial pressure in the measurement-object gas introduced through the third diffusion-rate limiting part 30 into the second internal cavity 40 is controlled to have a gradient that is always constant. In use as the NOx sensor, the oxygen concentration in the second internal space 40 is maintained at a constant value of approximately 0.001 ppm by the action of the main pump cell 21 and the auxiliary pump cell 50. That is to say, the oxygen concentration in the measurement-object gas introduced through the fourth diffusion-rate limiting part 60 into the third internal space 61 is considered to be maintained at a constant value of approximately 0.001 ppm.

The drive control part 92 has: an electromotive force measurement mode in which the main pump cell 21 and the auxiliary pump cell 50 that function as the adjustment pump cell is operated as described above and the current measurement pump cell 41 is not operated to detect a concentration of the target gas to be measured in the measurement-object gas based on an electromotive force value (the open electromotive force V2open) in the electromotive force detection sensor cell 82; and a current measurement mode in which the main pump cell 21, the auxiliary pump cell 50 and the current measurement pump cell 41 are operated to detect a concentration of the target gas to be measured in the measurement-object gas based on a current value (the pump current Ip2) in the current measurement pump cell 41.

In the electromotive force measurement mode, the switching unit 47 prevents a current from flowing through the current measurement pump cell 41. The measurement-object gas whose oxygen concentration has been adjusted to the predetermined concentration in the main pump cell 21 and the auxiliary pump cell 50 is introduced into the third internal cavity 61. In the measurement electrode 44, nitrogen oxide in the measurement-object gas is reduced to generate oxygen. In the electromotive force measurement mode, the generated oxygen remains around the measurement electrode 44 without being pumped out by the current measurement pump cell 41. In the electromotive force detection sensor cell 82, the open electromotive force V2open is generated corresponding to the difference between the amount of oxygen generated by the reduction of the NOx component in the atmosphere around the measurement electrode 44 and the amount of oxygen contained in the reference air. The drive control part 92 detects the open electromotive force V2open generated in the electromotive force detection sensor cell 82. As such, in the electromotive force measurement mode, a current does not flow through the current measurement pump cell 41, that is, an electromotive force generated in the electromotive force detection sensor cell 82 is the open electromotive force V2open. In this specification, the electromotive force measurement mode is also denoted as an open electromotive force measurement mode.

In the current measurement mode, the switching unit 47 allow a current to flow through the current measurement pump cell 41. In the current measurement mode, the drive control part 92 continues to acquire the electromotive force V2 detected in the electromotive force detection sensor cell 82. In the current measurement mode, the drive control part 92 performs feedback control of the pump voltage Vp2 of the variable power supply 46 in the current measurement pump cell 41 so that the electromotive force V2 detected in the electromotive force detection sensor cell 82 is at a constant value (referred to as a set value $V2_{SET}$). The set value $V2_{SET}$ is set in advance as a value such that the oxygen concentration around the measurement electrode 44 in the third internal cavity 61 is a predetermined low concentration. The measurement-object gas whose oxygen concentration has been adjusted to the predetermined concentration in the main pump cell 21 and the auxiliary pump cell 50 is introduced into the third internal cavity 61. In the measurement electrode 44, nitrogen oxide in the measurement-object gas is reduced to generate oxygen. Substantially all of the generated oxygen is pumped out by the drive control part 92, which applies the pump current Ip2 to the current measurement pump cell 41. The set value $V2_{SET}$ can be set as a value such that substantially all of NOx is decomposed in the measurement electrode 44. By setting the set value $V2_{SET}$ in this way, substantially all of NOx in the measurement-object gas is detected as the pump current Ip2 in the measurement electrode 44. In the current measurement mode, the electromotive force V2 detected in the electromotive force detection sensor cell 82 is used, as a control voltage, for the feedback control of the pump voltage Vp2 of the variable power supply 46 in the current measurement pump cell 41.

Figure 3:
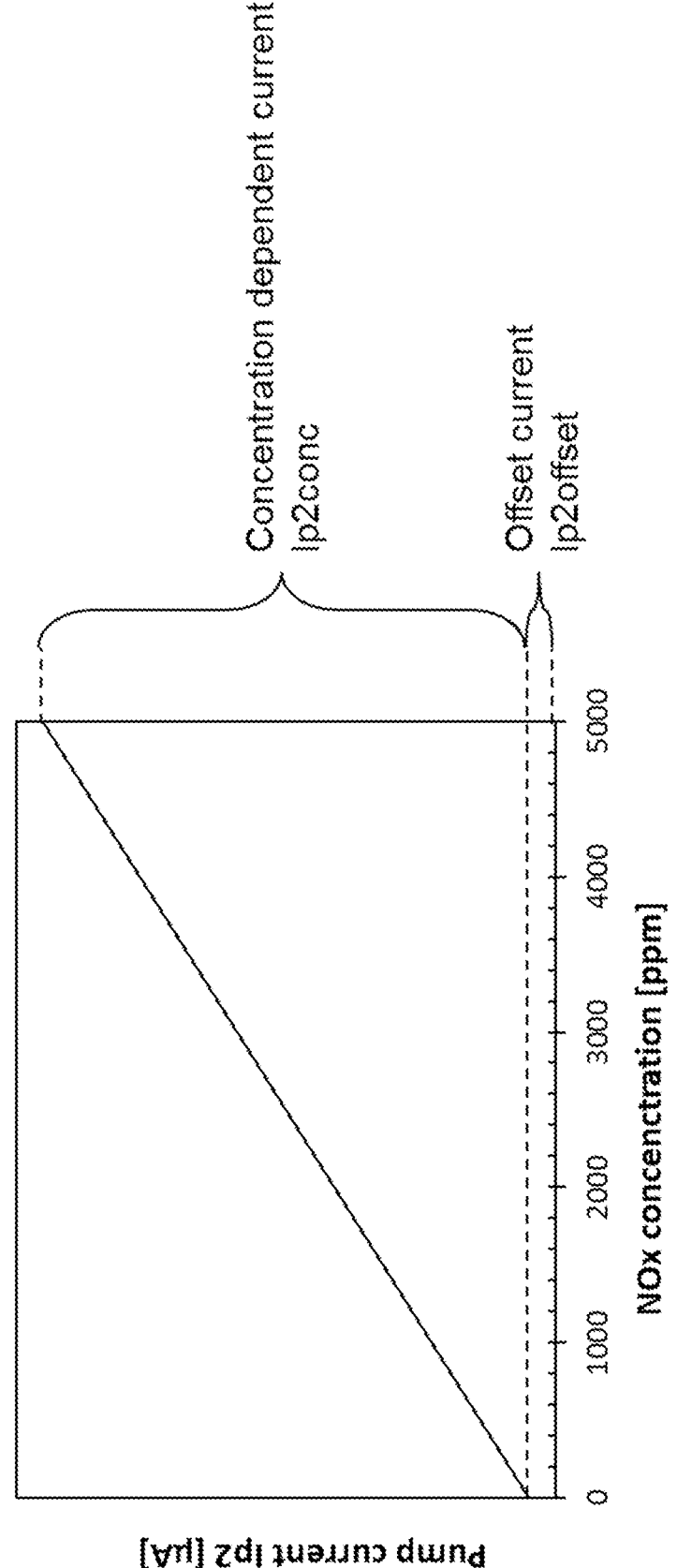
FIG. 3 is a graph schematically showing one example of a relationship between NOx concentration and a pump current Ip2 in the gas sensor 100. The horizontal axis of the graph represents the NOx concentration (ppm) and the vertical axis of the graph represents a value of the pump current Ip2 (μA).

Here, the pump current Ip2 detected in the current measurement mode is described in detail. FIG. 3 is a graph schematically showing one example of a relationship between NOx concentration in the measurement-object gas and the pump current Ip2 in the gas sensor 100. The horizontal axis of the graph represents the NOx concentration (ppm) and the vertical axis of the graph represents a value of the pump current Ip2 (μA).

As described above, in the current measurement mode, substantially all of the oxygen generated by the reduction of nitrogen oxide is pumped out by the drive control part 92, which applies the pump current Ip2 to the current measurement pump cell 41. Therefore, the pump current Ip2 is a current value corresponding to the amount of the oxygen generated by the reduction of nitrogen oxide. The amount of the oxygen generated by the reduction of nitrogen oxide is proportional to the amount of reduced nitrogen oxide. When substantially all of nitrogen oxide in the measurement-object is decomposed in the measurement electrode 44, the amount of the oxygen generated by the reduction of nitrogen oxide is proportional to the concentration of nitrogen oxide (NOx concentration). That is, as shown in FIG. 3, a linear relationship exists between NOx concentration and the pump current Ip2 over a wide range of NOx concentration. Based on this linear relationship between NOx concentration and the pump current Ip2, the gas sensor 100 can measure NOx concentration in the wide concentration range.

As shown in FIG. 3, the pump current Ip2 includes an offset current Ip2offset that flows regardless of NOx concentration, and a concentration dependent current Ip2conc that flows corresponding to NOx concentration. The concentration dependent current Ip2conc is a current that flows corresponding to an amount of oxygen generated by the reduction of nitrogen oxide, and a current value of the concentration dependent current Ip2conc is roughly proportional to the NOx concentration.

The offset current Ip2offset is a current that flows regardless of NOx concentration. The offset current Ip2offset is a current that is generated by factors other than oxygen generated by the decomposition of NOx that is a target gas to be measured. The offset current Ip2offset is considered to include a current that is caused by a residual oxygen in the measurement-object gas whose oxygen concentration has been adjusted to the predetermined concentration in the main pump cell 21 and the auxiliary pump cell 50, an oxygen generated by decomposition of a part of water ($H_2O$) in the measurement-object gas at the measurement electrode 44, and the like. The offset current Ip2offset is also considered to include a leakage current from the heater 72 that is energized to heat the gas sensor 100, a current due to transfer of a charge such as an electron and an impurity contained in the measurement electrode 44, the outer pump electrode 23, and the solid electrolyte layers (in FIG. 1, the second solid electrolyte layer 6, the spacer layer 5, and the first solid electrolyte layer 4) that constitute the current measurement pump cell 41, and the like.

If the current value of the offset current Ip2offset changes for some reasons while the gas sensor 100 is detecting the NOx concentration in the measurement-object gas, the pump current Ip2 detected in the current measurement pump cell 41 shifts by a change amount ΔIp2offset of the offset current Ip2offset, regardless of the NOx concentration in the measurement-object gas. The offset current Ip2offset is considered to change due to, for example, change in the electrode temperature by change in the measurement-object gas temperature, and change in the output of heater power supply 77 therewith. The offset current Ip2offset is also considered to change due to change in $H_2O$ concentration in the measurement-object gas.

In case of measuring the measurement-object gas that contains high concentration of NOx, the pump current Ip2 detected in the current measurement pump cell 41 is relatively large so that the change in the pump current Ip2 due to the change ΔIp2offset of the offset current Ip2offset is relatively small. Therefore, even if the offset current Ip2offset changes, NOx concentration can be measured with higher measurement accuracy. For example, if the change ΔIp2offset of the offset current Ip2offset corresponds to 5 ppm in terms of NOx concentration, the measurement error is 10% when the measurement-object gas with NOx concentration of 50 ppm is measured, but the measurement error is 1% when the measurement-object gas with NOx concentration of 500 ppm is measured.

On the other hand, for measuring the measurement-object gas that contains low concentration of NOx, it is preferred that an effect of the change of the offset current Ip2offset is reduced.

The offset current Ip2offset is generated when the pump voltage Vp2 of the variable power supply 46 is applied in the current measurement pump cell 41 so that the pump current Ip2 flows. Accordingly, when the pump voltage Vp2 is not applied in the current measurement pump cell 41, the pump current Ip2 does not flow so that the offset current Ip2offset is not generated. In the gas sensor 100, by turning off the switching unit 47 to cut off the electrical connection in the current measurement pump cell 41 so that a current does not flow through the current measurement pump cell 41, a state in which the offset current Ip2offset is not generated can be realized. In this case, the drive control part 92 performs the control in the open electromotive force measurement mode, and detects the open electromotive force V2open in the electromotive force detection sensor cell 82.

Figure 4:
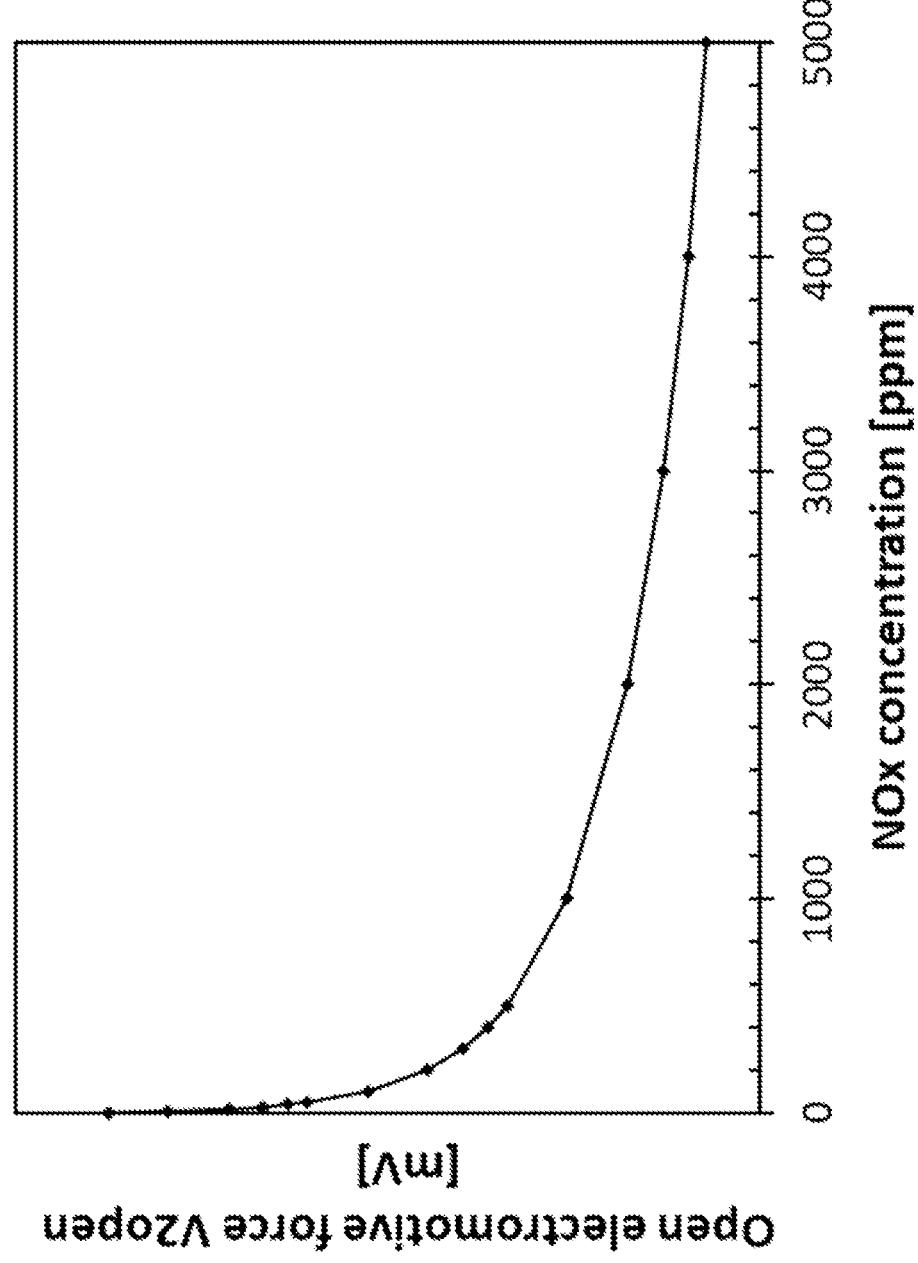
FIG. 4 is a graph schematically showing one example of a relationship between NOx concentration and an open electromotive force V2open in the gas sensor 100. The horizontal axis of the graph represents the NOx concentration (ppm) and the vertical axis of the graph represents a value of the open electromotive force V2open (mV).

The open electromotive force V2open in the electromotive force detection sensor cell 82 will be described in detail. FIG. 4 is a graph schematically showing one example of a relationship between NOx concentration and the open electromotive force V2open in the gas sensor 100. The horizontal axis of the graph represents the NOx concentration (ppm) and the vertical axis of the graph represents a value of the open electromotive force V2open (mV).

In the electromotive force measurement mode, as described above, the electrical connection of the current measurement pump cell 41 is cut off so that a current does not flow. In this case, in the electromotive force detection sensor cell 82, the open electromotive force V2open is generated corresponding to the difference between the amount of oxygen generated by the reduction of the NOx component in the atmosphere around the measurement electrode 44 and the amount of oxygen contained in the reference air. A relationship as shown in FIG. 4 exists between the open electromotive force V2open and NO concentration.

In the electromotive force measurement mode, the gas sensor 100 is in a state where the pump current Ip2 does not flow, so the offset current Ip2offset is not generated. Therefore, NOx concentration can be measured accurately based on the relationship between the NOx concentration and the open electromotive force V2open as shown in FIG. 4, without being affected by the offset current Ip2offset.

As shown in FIG. 4, the lower the NO concentration in the measurement-object gas is, the larger the change of the open electromotive force V2open with respect to the NO concentration change is. That is, the lower the NO concentration in the measurement-object gas is, the more greatly the open electromotive force V2open changes with respect to a minute change in the NO concentration, and therefore resolution of the measurement is tend to be higher. Thus, in case of measuring the measurement-object gas that contains low concentration of NOx, NOx concentration can be measured with particularly high measurement accuracy.

As such, in the electromotive force measurement mode, the offset current Ip2offset is not generated so that NOx concentration can be measured accurately in the wide concentration range without being affected by the offset current Ip2offset. Specifically, in case of measuring the measurement-object gas that contains low concentration of NOx, the change of the open electromotive force V2open with respect to the minute change in the NOx concentration is large, and therefore the resolution of the measurement is tend to be higher. Accordingly, in case of measuring the measurement-object gas that contains low concentration of NOx, NOx concentration can be measured with particularly high measurement accuracy.

In the current measurement mode, the linear relationship as shown in FIG. 3 exists between the pump current Ip2 and NOx concentration over the wide range of NOx concentration, so that NOx concentration can be measured accurately in the wide concentration range. Specifically, in case of measuring the measurement-object gas that contains high concentration of NOx, the change in the pump current Ip2 due to the change ΔIp2offset of the offset current Ip2offset is relatively small. Therefore, NOx concentration can be measured with higher measurement accuracy.

The concentration calculating part 93 is configured to calculate and output a NOx concentration in a measurement-object gas.

In the electromotive force measurement mode, the concentration calculating part 93 acquires the open electromotive force V2open in the electromotive force detection sensor cell 82, calculates the NOx concentration in the measurement-object gas on the basis of a previously-stored conversion parameter (open electromotive force-concentration conversion parameter) between the open electromotive force V2open and the NOx concentration in the measurement-object gas, and outputs the NOx concentration as a measurement value of the gas sensor 100. The open electromotive force-concentration conversion parameter is previously stored, as data showing the relationship as illustrated in FIG. 4, in the memory of the control part 91 which functions as the concentration calculating part 93. The electromotive force-concentration conversion parameter may appropriately be determined by those skilled in the art by, for example, previously performing an experiment on the gas sensor 100. The electromotive force-concentration conversion parameter may be, for example, the coefficient of an approximate expression (e.g., logarithmic function) obtained by experiment or a map showing the relationship between the open electromotive force V2open and the NOx concentration in the measurement-object gas. The electromotive force-concentration conversion parameter may be specific to each individual gas sensor 100 or may be common to a plurality of gas sensors.

In the current measurement mode, the concentration calculating part 93 acquires the pump current Ip2 in the current measurement pump cell 41, calculates the NOx concentration in a measurement-object gas on the basis of a previously-stored conversion parameter (current-concentration conversion parameter) between the pump current Ip2 and the NOx concentration in the measurement-object gas, and outputs the NOx concentration as a measurement value of the gas sensor 100. The current-concentration conversion parameter is previously stored, as data showing the linear relationship as illustrated in FIG. 3, in the memory of the control part 91 which functions as the concentration calculating part 93. The current-concentration conversion parameter may appropriately be determined by those skilled in the art by, for example, previously performing an experiment on the gas sensor 100. The current-concentration conversion parameter may be, for example, the coefficient of an approximate expression (e.g., linear function) obtained by experiment or a map showing the relationship between the pump current Ip2 and the NOx concentration in a measurement-object gas. The current-concentration conversion parameter may be specific to each individual gas sensor 100 or may be common to a plurality of gas sensors.

The measurement mode switching part 94 is configured to perform switching between the electromotive force measurement mode and the current measurement mode that are described above.

The measurement mode switching part 94 switches the switching unit so that a current does not flow or does not substantially flow through the current measurement pump cell 41 in case of switching from the current measurement mode to the electromotive force measurement mode. In this embodiment, the measurement mode switching part 94 outputs a control signal to the switching unit 47 to be OFF. Further, the measurement mode switching part 94 gives instructions to the drive control part 92 to perform the control in the electromotive force measurement mode. In this case, the drive control part 92 does not perform the above-described feedback control to the pump voltage Vp2 of the variable power supply 46 in the current measurement pump cell 41, and detects the open electromotive force V2open in the electromotive force detection sensor cell 82. The measurement mode switching part 94 gives instructions to the concentration calculating part 93 to acquire the open electromotive force V2open in the electromotive force detection sensor cell 82, and calculate the NOx concentration on the basis of the electromotive force-concentration conversion parameter.

The measurement mode switching part 94 switches the switching unit so that a current flows through the current measurement pump cell 41 in case of switching from the electromotive force measurement mode to the current measurement mode. In this embodiment, the measurement mode switching part 94 outputs a control signal to the switching unit 47 to be ON. Further, the measurement mode switching part 94 gives instructions to the drive control part 92 to perform the control in the current measurement mode. In this case, the drive control part 92 performs the above-described feedback control to the pump voltage Vp2 of the variable power supply 46 in the current measurement pump cell 41, and detects the pump current Ip2 in the current measurement pump cell 41. The measurement mode switching part 94 gives instructions to the concentration calculating part 93 to acquire the pump current Ip2 in the current measurement pump cell 41, and calculate the NOx concentration on the basis of the current-concentration conversion parameter.

Switching between the electromotive force measurement mode and the current measurement mode may be performed on the basis of NOx concentration output by the concentration calculating part 93. The measurement mode switching part 94 (more specifically, the memory that functions as the measurement mode switching part 94 in the control unit 91) stores in advance, a first concentration threshold value C1 that is a threshold value for switching from the current measurement mode to the electromotive force measurement mode, and a second concentration threshold value C2 that is a threshold value for switching from the electromotive force measurement mode to the current measurement mode. The measurement mode switching part 94 may continuously acquire the NOx concentration output by the concentration calculating part 93, or may acquire the NOx concentration output by the concentration calculating part 93 at predetermined intervals.

The measurement mode switching part 94 acquires the NOx concentration output by the concentration calculating part 93 in the current measurement mode, and switches to the electromotive force measurement mode when the measurement mode switching part 94 determines that NOx concentration is in a low concentration range where NOx concentration is lower than a predetermined first concentration threshold value C1. The measurement mode switching part 94 maintains the current measurement mode when the measurement mode switching part 94 determines that the NOx concentration is equal to or higher than the predetermined first concentration threshold value C1.

The measurement mode switching part 94 also acquires the NOx concentration output by the concentration calculating part 93 in the electromotive force measurement mode, and switches to the current measurement mode when the measurement mode switching part 94 determines that NOx concentration is in a high concentration range where NOx concentration is higher than a predetermined second concentration threshold value C2. The measurement mode switching part 94 maintains the electromotive force measurement mode when the measurement mode switching part 94 determines that the NOx concentration is equal to or lower than the predetermined second concentration threshold value C2.

The first concentration threshold value C1 that is the threshold value for switching from the current measurement mode to the electromotive force measurement mode may appropriately be determined by a person skilled in the art. The first concentration threshold value C1 may be a different value depending on the assumed concentration range of NOx in the measurement-object gas and the measurement accuracy required for the gas sensor 100. The first concentration threshold value C1 may be a lower limit of the NOx concentration at which a desired measurement accuracy can be obtained when measuring in the current measurement mode. The first concentration threshold value C1 may be, for example, a lower limit of the NOx concentration at which a value of the offset current Ip2offset is in an acceptable range in terms of measurement accuracy. Alternatively, the first concentration threshold value C1 may be, for example, a lower limit of the NOx concentration at which a value of the change ΔIp2offset of the offset current Ip2offset is in an acceptable range in terms of measurement accuracy. The first concentration threshold value C1 may be, for example, in a rage of 50 ppm to 500 ppm. For example, the first concentration threshold value C1 may be 100 ppm.

The second concentration threshold value C2 that is the threshold value for switching from the electromotive force measurement mode to the current measurement mode may appropriately be determined by a person skilled in the art. The second concentration threshold value C2 may be a different value depending on the assumed concentration range of NOx in the measurement-object gas and the measurement accuracy required for the gas sensor 100. The second concentration threshold value C2 may be an upper limit of the NOx concentration at which a desired measurement accuracy can be obtained when measuring in the electromotive force measurement mode. The second concentration threshold value C2 may be, for example, an upper limit of the NOx concentration at which a change amount of the open electromotive force V2open with respect to a change amount of the NO concentration is in an acceptable range in terms of the resolution of the measurement. The second concentration threshold value C2 may be, for example, in a rage of 50 ppm to 500 ppm. For example, the second concentration threshold value C2 may be 300 ppm.

The first concentration threshold value C1 and the second concentration threshold value C2 may be the same value, or may be different from each other. When the first concentration threshold value C1 and the second concentration threshold value C2 are the same value, the electromotive force measurement mode is executed in the low concentration range where NOx concentration is lower than the first concentration threshold value C1 (=the second concentration threshold value C2), and the current measurement mode is executed in the high concentration range where NOx concentration is equal to or higher than the first concentration threshold value C1 (=the second concentration threshold value C2).

It is more preferred that the first concentration threshold value C1 is lower than the second concentration threshold value C2. In other words, it is more preferred that two threshold values that have a concentration range are used.

Figure 5:
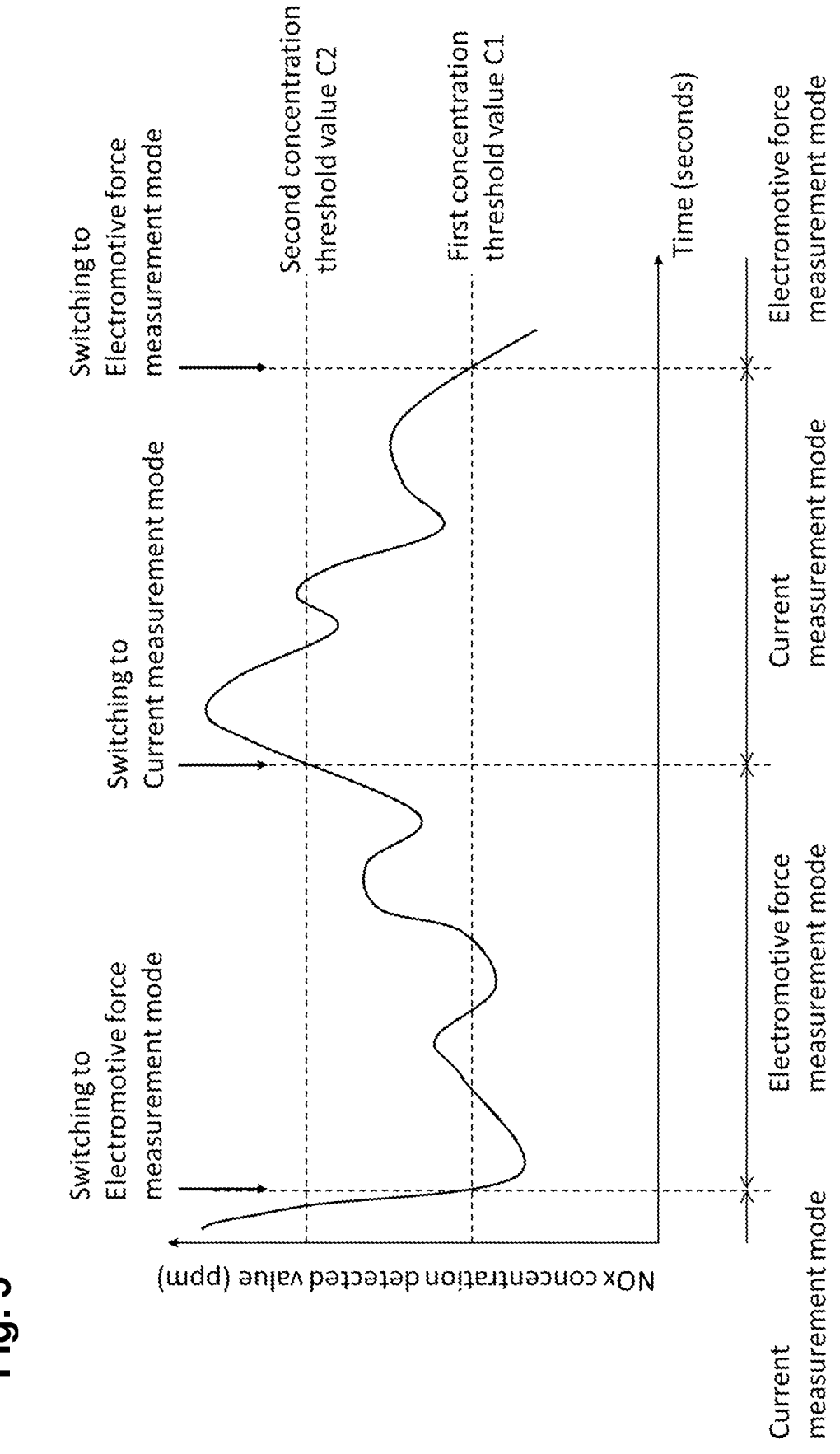
FIG. 5 is a graph schematically showing one example of time variation of NOx concentration detected value output by the gas sensor 100 and switching of measurement modes. The horizontal axis of the graph represents time (seconds) and the vertical axis of the graph represents the NOx concentration detected value (ppm) output by the gas sensor 100.

FIG. 5 is a graph schematically showing one example of time variation of NOx concentration detected value output by the gas sensor 100 and switching of the measurement modes. The horizontal axis of the graph represents time (seconds) and the vertical axis of the graph represents the NOx concentration detected value (ppm) output by the gas sensor 100.

As shown in FIG. 5, when NOx concentration in the measurement-object gas (i.e., NOx concentration output by the gas sensor 100) falls below the first concentration threshold value C1, the measurement mode is switched to the electromotive force measurement mode. Even if the NOx concentration in the measurement-object gas fluctuates around the first concentration threshold value C1 and exceeds the first concentration threshold value C1 after switching to the electromotive force measurement mode, the electromotive force measurement mode is continued without switching to the current measurement mode until the NOx concentration in the measurement-object gas exceeds the second concentration threshold value C2. After that, when the NOx concentration in the measurement-object gas exceeds the second concentration threshold value C2, the measurement mode is switched to the current measurement mode. Even if the NOx concentration in the measurement-object gas fluctuates around the second concentration threshold value C2 and falls below the second concentration threshold value C2 after switching to the current measurement mode, the current measurement mode is continued without switching to the electromotive force measurement mode until the NOx concentration in the measurement-object gas falls below the first concentration threshold value C1.

Thus, when the first concentration threshold value C1 is lower than the second concentration threshold value C2, the concentration range (intermediate concentration range) between the first concentration threshold value C1 and the second concentration threshold value C2 serves as a buffer range where the most recent measurement mode continues to be maintained without switching measurement modes. That is, when the NOx concentration in the measurement-object gas frequently fluctuates around the first concentration threshold value C1 or the second concentration threshold value C2, switching of the measurement modes can be adjusted not to be too frequent. At the time of switching the measurement mode, the control of the current measurement pump cell 41 is changed, and thereby a situation where the gas sensor 100 cannot measure NOx concentration temporarily may occur. By providing the buffer range between the first concentration threshold value C1 and the second concentration threshold value C2, switching of the measurement modes can be adjusted not to occur too frequent. Accordingly, the gas sensor 100 can measure NOx concentration more continuously and accurately.

For example, the first concentration threshold value C1 may be 50 ppm to 200 ppm, and the second concentration threshold value C2 may be 200 ppm to 500 ppm. For example, the first concentration threshold value C1 may be 100 ppm, and the second concentration threshold value C2 may be 300 ppm.

The measurement mode may be switched in the buffer range between the first concentration threshold value C1 and the second concentration threshold value C2. The measurement mode may be switched, for example, by predicting NOx concentration detected value based on time variation of the NOx concentration detected value (slope of the graph in FIG. 5). The measurement mode may be switched, for example, based on the time for which the NOx concentration detected value is within the buffer range.

[Detection of Concentration of Target Gas to be Measured]

Next, a method for measuring a concentration of the target gas to be measured in the measurement-object gas by using the gas sensor 100 will be described.

A control method of the gas sensor of the present embodiment includes:

a concentration detecting step of performing an electromotive force measurement mode in which the adjustment pump cell is operated and the current measurement pump cell is not operated to detect a concentration of the target gas to be measured in the measurement-object gas based on an electromotive force value in the electromotive force detection sensor cell, or a current measurement mode in which the adjustment pump cell and the current measurement pump cell are operated to detect a concentration of the target gas to be measured in the measurement-object gas based on a current value in the current measurement pump cell, while switching between the electromotive force measurement mode and the current measurement mode by using the switching unit. In the concentration detecting step, any one of the measurement modes is always executed to continuously detect the concentration. It is to be noted that, in this embodiment, the main pump cell 21 and the auxiliary pump cell 50 function as the adjustment pump cells.

The detecting process of NOx concentration in the gas sensor 100 of this embodiment will be described below in detail. FIG. 6 is a flow chart showing one example of detecting process of NOx concentration in the gas sensor 100.

The detecting process of NOx concentration is started when, for example, the gas sensor 100 receives a start signal (Dew point). When the gas sensor 100 is installed in a car or the like, the start signal (Dew point) is, for example, a signal sent from an ECU, an exhaust gas treatment system, or the like of the car to the gas sensor 100. The detecting process of NOx concentration may be started by, for example, manually turning on the power supply of the control unit 90.

When the detecting process of NOx concentration is started, the drive control part 92 of the control part 91 starts to heat the heater 72 by the application of power to the heater 72 (step S10), and the sensor element 101 is maintained at a driving temperature (e.g., about 800° C.) at which the concentration of NOx is measured with high accuracy due to the activation of the solid electrolyte.

Next, the drive control part 92 starts to control the main pump cell 21 (step S11), and also starts to control the auxiliary pump cell 50 (step S12). Specifically, the feedback control based on the set value $Ip1_{SET}$ and the set value $V0_{SET}$ is performed for the main pump cell 21, and the feedback control based on the set value $V1_{SET}$ is performed for the auxiliary pump cell 50. Either of the steps S11 and S12 may be performed first, or the steps S11 and S12 may be performed simultaneously. The steps S11 and S12 may be performed after the sensor element 101 reaches the driving temperature, or may be performed at a temperature lower than the driving temperature.

The measurement-object gas passes through the gas inlet 10, the first diffusion-rate limiting part 11, the buffer space 12, and the second diffusion-rate limiting part 13 in this order, and reaches the first internal cavity 20 so that the oxygen concentration is adjusted by the action of the main pump cell 21. Then, the measurement-object gas passes through the third diffusion-rate limiting part 30, and reaches the second internal cavity 40 so that the oxygen concentration is further adjusted by the action of the auxiliary pump cell 50. The measurement-object gas whose oxygen concentration has been adjusted by the main pump cell 21 and the auxiliary pump cell 50 passes through the fourth diffusion-rate limiting part 60, and reaches the third internal cavity 61.

Next, the measurement mode switching part 94 of the control part 91 performs switching to the current measurement mode (step S13). Specifically, the measurement mode switching part 94 outputs a control signal to the switching unit 47 as an example of the switching unit to be ON. Further, the measurement mode switching part 94 gives instructions to the drive control part 92 to perform the control in the current measurement mode. In this case, the drive control part 92 performs the feedback control to the pump voltage Vp2 of the variable power supply 46 in the current measurement pump cell 41, and detects the pump current Ip2 in the current measurement pump cell 41. The measurement mode switching part 94 gives instructions to the concentration calculating part 93 to acquire the pump current Ip2 in the current measurement pump cell 41, and calculate the NOx concentration on the basis of the current-concentration conversion parameter. In the current measurement mode, as described above, the pump current Ip2 corresponding to the NOx concentration flows through the current measurement pump cell 41. The step S13 may be performed simultaneously with either or both of the above-described steps S11 and S12.

Then, the concentration calculating part 93 acquires the pump current Ip2 in the current measurement pump cell 41, and calculates the NOx concentration in the measurement-object gas on the basis of the previously-stored conversion parameter (current-concentration conversion parameter) between the pump current Ip2 and the NOx concentration in the measurement-object gas (step S14). The calculated NOx concentration is output as the detected value of the gas sensor 100. After the step S14, the measurement mode switching part 94 acquires the NOx concentration calculated by the concentration calculating part 93, and determines whether or not the acquired NOx concentration is lower than the first concentration threshold value C1 (step S15). As the first concentration threshold value C1, for example, the lower limit of the NOx concentration at which the desired measurement accuracy can be obtained when measuring in the current measurement mode is set in advance.

In the step S15, when the NOx concentration acquired from the concentration calculating part 93 is equal to or higher than the first concentration threshold value C1, the step S14 and subsequent processes are performed. That is, when the NOx concentration is equal to or higher than the first concentration threshold value C1, the measurement mode switching part 94 does not switch the measurement mode, and the drive control part 92 and the concentration calculating part 93 continue the current measurement mode.

In the step S15, when the NOx concentration acquired from the concentration calculating part 93 is lower than the first concentration threshold value C1, the measurement mode switching part 94 performs switching to the open electromotive force measurement mode (step S23). Specifically, the measurement mode switching part 94 outputs a control signal to the switching unit 47 to be OFF. Further, the measurement mode switching part 94 gives instructions to the drive control part 92 to perform the control in the open electromotive force measurement mode. In this case, the drive control part 92 does not perform the above-described feedback control to the pump voltage Vp2 of the variable power supply 46 in the current measurement pump cell 41, and detects the open electromotive force V2open in the electromotive force detection sensor cell 82. The measurement mode switching part 94 gives instructions to the concentration calculating part 93 to acquire the open electromotive force V2open in the electromotive force detection sensor cell 82, and calculate the NOx concentration on the basis of the open electromotive force-concentration conversion parameter. In the electromotive force measurement mode, the pump current Ip2 does not flow through the current measurement pump cell 41, and as described above, the open electromotive force V2open corresponding to the NOx concentration in the measurement-object gas is generated in the electromotive force detection sensor cell 82.

Then, the concentration calculating part 93 acquires the open electromotive force V2open in the electromotive force detection sensor cell 82, and calculates the NOx concentration in the measurement-object gas on the basis of the previously-stored conversion parameter (open electromotive force-concentration conversion parameter) between the open electromotive force V2open and the NOx concentration in the measurement-object gas (step S24). The calculated NOx concentration is output as the detected value of the gas sensor 100. After the step S24, the measurement mode switching part 94 acquires the NOx concentration calculated by the concentration calculating part 93, and determines whether or not the acquired NOx concentration is higher than the second concentration threshold value C2 (step S25). As the second concentration threshold value C2, for example, the upper limit of the NOx concentration at which the desired measurement accuracy can be obtained when measuring in the open electromotive force measurement mode is set in advance.

In the step S25, when the NOx concentration acquired from the concentration calculating part 93 is equal to or lower than the second concentration threshold value C2, the step S24 and subsequent processes are performed. That is, when the NOx concentration is equal to or lower than the second concentration threshold value C2, the measurement mode switching part 94 does not switch the measurement mode, and the drive control part 92 and the concentration calculating part 93 continue the open electromotive force measurement mode.

In the step S25, when the NOx concentration acquired from the concentration calculating part 93 is higher than the second concentration threshold value C2, the measurement mode switching part 94 performs switching to the current force measurement mode (step S13), and the step S14 and subsequent processes are performed.

Accordingly, the control part 91 determines, in the measurement mode switching part 94, whether to use the current measurement mode or the electromotive force measurement mode based on the NOx concentration acquired from the concentration calculating part 93, and as a result, detects the NOx concentration by using either of the measurement modes. The NOx concentration can be measured more accurately in a wide concentration range including the low concentration, by properly using the electromotive force measurement mode in which the measurement-object gas containing the low concentration of NOx can be measured more accurately, and the current measurement mode in which the measurement-object gas containing the high concentration of NOx can be measured more accurately.

In the step S13, when the measurement mode switching part 94 switches from the open electromotive force measurement mode to the current measurement mode, the pump current Ip2 is applied to the current measurement pump cell 41 so that the electromotive force V2 detected in the electromotive force detection sensor cell 82 is at the set value V2$_{SET}$, thereby controlling the atmosphere in the vicinity of the measurement electrode 44 at a state where all of the oxygen derived from NOx is pumped out. In this state, the measurement of the NOx concentration in the current measurement mode (step S14) is performed at least once, and then the switching to the electromotive force measurement mode (step S23) is performed. Also, in the step S23, when the measurement mode switching part 94 switches from the current measurement mode to the open electromotive force measurement mode, the pump current Ip2 is not applied to the current measurement pump cell 41, thereby controlling the atmosphere in the vicinity of the measurement electrode 44 at a state where all of the oxygen derived from NOx exists. In this state, the measurement of the NOx concentration in the electromotive force measurement mode (step S24) is performed at least once, and then the switching to the current measurement mode (step S13) is performed.

As such, when the switching of the measurement mode is performed, the atmosphere in the vicinity of the measurement electrode 44 is controlled so that the NOx concentration can be measured, and then determination for the next switching of the measurement mode is performed. The switching of the measurement mode may usually be performed at intervals of one second or longer. The switching of the measurement mode is not intended to be the switching by turning on and off in such a minute time in which the above-described switching of the atmosphere in the vicinity of the measurement electrode 44 cannot be realized, that is, the on and off control by so-called pulse current.

Immediately after the measurement mode switching part 94 switches from the open electromotive force measurement mode to the current measurement mode in the step S13, the control of the current measurement pump cell 41 is changed so that the pump current Ip2 may not be stable in some cases. Thus, the concentration calculating part 93 may perform the step S14 after a predetermined waiting time has elapsed. Also, immediately after the measurement mode switching part 94 switches from the current measurement mode to the open electromotive force measurement mode in the step S23, the control of the current measurement pump cell 41 is changed so that the open electromotive force V2open may not be stable in some cases. Thus, the concentration calculating part 93 may perform the step S24 after a predetermined waiting time has elapsed.

The gas sensor 100 for detecting NOx concentration in a measurement-object gas has been described above as an example of the embodiment according to the present invention, but the present invention is not limited thereto. The present invention may include a gas sensor having any structure including a sensor element and a control unit as long as the object of the present invention can be achieved, that is, the target gas to be measured is accurately measured in a wide concentration range including the low concentration of the target gas to be measured.

In the above embodiment, a switch is provided as one example of the switching unit 47, but the present invention is not limited thereto. For example, the variable power supply 46 may be used as the switching unit 47. The measurement mode switching part 94 may set the pump voltage Vp2 in the variable power supply 46 to zero not to apply a voltage in the current measurement pump cell 41 so that a current does not flow through the current measurement pump cell 41 in case of switching to the electromotive force measurement mode, and may set the pump voltage Vp2 in the variable power supply 46 to a predetermined value to apply the predetermined voltage in the current measurement pump cell 41 so that a current flows through the current measurement pump cell 41 in case of switching to the current measurement mode. It is to be noted that, in the current measurement mode, the feedback control may be performed to the pump voltage Vp2 of the variable power supply 46 in the current measurement pump cell 41 so that the electromotive force V2 as the control voltage detected in the electromotive force detection sensor cell 82 is at the set value $V2_{SET}$, as in the case of the above embodiment.

In the above embodiment, the measurement mode switching part 94 first switches to the current measurement mode in the step S13 after the step S12, but the measurement mode switching part 94 may first switch to the electromotive force measurement mode in the step S23 after the step S12.

Alternatively, at a startup of the gas sensor 100, the control unit 90 may be preset in the current measurement mode, or may be preset in the electromotive force measurement mode.

At the startup of the gas sensor 100, the inside of the third internal cavity 61 is filled with the measurement-object gas, and the oxygen concentration in the measurement-object gas in the inside of the third internal cavity 61 is often higher than that in the state where the drive control is steadily being performed. In case of controlling in the current measurement mode at the startup, the current measurement pump cell 41 is operated in addition to the main pump cell 21 and the auxiliary pump cell 50. As a result, the oxygen in the measurement-object gas in the inside of the third internal cavity 61 is actively pumped out, and the state where the drive control is steadily being performed can be obtained more quickly. That is, the time from when the gas sensor 100 is started until when the NOx concentration can be measured (light-off time) can be reduced.

In the above embodiment, the measurement mode switching part 94 switches between the electromotive force measurement mode and the current measurement mode based on the NOx concentration calculated by the concentration calculating part 93. However, the present invention is not limited thereto.

As a threshold value for switching from the current measurement mode to the electromotive force measurement mode, instead of the first concentration threshold value C1, a lower limit of the pump current Ip2 at which a desired measurement accuracy can be obtained when measuring in the current measurement mode may appropriately be set by a person skilled in the art. As a threshold value for switching from the electromotive force measurement mode to the current measurement mode, instead of the second concentration threshold value C2, an upper limit of the open electromotive force V2open at which a desired measurement accuracy can be obtained when measuring in the electromotive force measurement mode may appropriately be set by a person skilled in the art.

The switching between the electromotive force measurement mode and the current measurement mode may be performed, for example, based on a signal sent from other devices such as the ECU and the exhaust gas treatment system of the car.

In the gas sensor 100 of the above embodiment, the current measurement pump cell 41 and the electromotive force detection sensor cell 82 are configured as separate electrochemical cells. However, the present invention is not limited thereto. For example, a current measurement pump cell may be configured as a pump cell between the measurement electrode 44 and the reference electrode 42. That is, the reference electrode 42 may function as an outer measurement electrode in the current measurement pump cell. Referring to the sensor element 101 of FIG. 1, a current measurement pump cell may be composed of the measurement electrode 44, the first solid electrolyte layer 4, the third substrate layer 3, and the reference electrode 42. The reference electrode 42 is disposed inside the base part 102. However, on the basis of the measurement electrode 44 disposed on the inner surface of the measurement-object gas flow part 15, the reference electrode 42 is disposed at a position different from the measurement-object gas flow part

15 and may be used as the outer measurement electrode. In this case, the control unit is also equipped with a switching unit for switching whether a current flows through the current measurement pump cell or not.

In this case, in the electromotive force measurement mode, the switching unit is switched so that a current does not flow through the current measurement pump cell, and the open electromotive force V2open between the measurement electrode 44 and the reference electrode 42 is detected. Then, NOx concentration is detected on the basis of the open electromotive force V2open. In the current measurement mode, the switching unit is switched so that a current flows through the current measurement pump cell, and a pump current flows between the measurement electrode 44 and the reference electrode 42 by applying a certain pump voltage between the measurement electrode 44 and the reference electrode 42. NOx concentration is detected on the basis of the pump current.

In the above embodiment, the gas sensor 100 detects the NOx concentration in a measurement-object gas. However, the target gas to be measured is not limited to NOx. For example, the target gas to be measured may be an oxide gas other than NOx (e.g., carbon dioxide $CO_2$, water $H_2O$). When the target gas to be measured is an oxide gas, in the current measurement mode, as in the case of the above embodiment in which the NOx concentration is detected, a measurement-object gas containing an oxide gas itself is introduced into the third internal cavity 61, and the oxide gas in the measurement-object gas is reduced at the measurement electrode 44 so that oxygen is generated. The generated oxygen is detected as the pump current Ip2 in the current measurement pump cell 41.

Carbon dioxide $CO_2$ and water $H_2O$ are reduced to generate a reducing gas such as carbon monoxide CO and hydrogen $H_2$, respectively, and oxygen $O_2$. In the electromotive force measurement mode, by setting the set value $V0_{SET}$ used for controlling the main pump cell 21 and the set value $V1_{SET}$ used for controlling the auxiliary pump cell 50 to larger values than those in the case of NOx, the oxygen concentration in the measurement-object gas is controlled to a lower concentration, and carbon dioxide $CO_2$ or water $H_2O$ is reduced (decomposed) in at least one of the inner main pump electrode 22 and the auxiliary pump electrode 51. As a result, the reducing gas generated by reduction of carbon dioxide $CO_2$ or water $H_2O$ and the oxygen (residual oxygen) whose concentration has been adjusted by the main pump cell 21 and the auxiliary pump cell 50 reach the measurement electrode 44. At this time, by controlling the concentration of the residual oxygen in the measurement-object gas so that a ratio of the residual oxygen to the reducing gas (rich gas) is near the theoretical air fuel ratio (stoichiometric) point, a concentration of the reducing gas (rich gas) derived from carbon dioxide $CO_2$ or water $H_2O$ can be detected as the open electromotive force V2open in the electromotive force detection sensor cell 82. In the range near the theoretical air fuel ratio (stoichiometric) point, as compared to other ranges, the open electromotive force V2open changes more greatly with respect to a minute change in the concentration of the rich gas, so that low concentration of the reducing gas (rich gas) derived from carbon dioxide $CO_2$ or water $H_2O$ can be detected.

In the above embodiment for detecting NOx concentration, for example, the set value $V2_{SET}$ used for controlling the main pump cell 21 may be set to about 150 mV to 450 mV, and the set value $V1_{SET}$ used for controlling the auxiliary pump cell 50 may be set to about 150 mV to 450 mV. On the other hand, in case of measuring carbon dioxide $CO_2$ or water $H_2O$, for example, the set value $V2_{SET}$ used for controlling the main pump cell 21 may be set to about 450 mV to 1000 mV, and the set value $V1_{SET}$ used for controlling the auxiliary pump cell 50 may be set to about 450 mV to 1000 mV. Accordingly, the set value $V0_{SET}$ used for controlling the main pump cell 21, and the set value $V1_{SET}$ used for controlling the auxiliary pump cell 50 may appropriately be set depending on a kind of the target gas to be measured. Further, the set value $Ip1_{SET}$ used for controlling the auxiliary pump cell 50 and the set value $V2_{SET}$ used for controlling the current measurement pump cell 41 in current measurement mode may appropriately be set depending on a kind of the target gas to be measured.

Alternatively, the target gas to be measured may be a non-oxide gas such as ammonia $NH_3$. When the target gas to be measured is a non-oxide gas, the non-oxide gas is converted to an oxide gas (for example, in the case of ammonia $NH_3$, $NH_3$ is converted to NO), and a measurement-object gas containing the converted oxide gas is introduced into the third internal cavity 61. At the measurement electrode 44, the converted oxide gas in the measurement-object gas is reduced so that oxygen is generated. The generated oxygen is detected as the open electromotive force V2open in the electromotive force detection sensor cell 82 in the electromotive force measurement mode, and is detected as the pump current Ip2 in the current measurement pump cell 41 in current measurement mode. The conversion from the non-oxide gas to the oxide gas can be performed by allowing at least one of the inner main pump electrode 22 and the auxiliary pump electrode 51 to function as a catalyst.

In the above embodiment, the drive control part 92 of the control part 91 performs feedback control for setting a set value $V0_{SET}$ of the electromotive force V0 in the oxygen-partial-pressure detection sensor cell 80 for main pump control on the basis of the pump current Ip1 in the auxiliary pump cell 50 so that the pump current Ip1 becomes a set value $Ip1_{SET}$, and performs feedback control of the pump voltage Vp0 of the variable power supply 24 in the main pump cell 21 so that the electromotive force V0 becomes the set value $V0_{SET}$. However, the control method is not limited thereto. For example, the drive control part 92 may perform feedback control of the pump voltage Vp0 of the variable power supply 24 in the main pump cell 21 so that the pump current Ip1 in the auxiliary pump cell 50 becomes a set value $Ip1_{SET}$. That is, the drive control part 92 may perform direct feedback control of the pump voltage Vp0 on the basis of the pump current Ip1 without acquiring the electromotive force V0 in the oxygen-partial-pressure detection sensor cell 80 for main pump control or setting the set value $V0_{SET}$.

In the gas sensor 100 of the above embodiment, as shown in FIG. 1, the sensor element 101 has a structure in which three internal cavities, the first internal cavity 20, the second internal cavity 40, and the third internal cavity 61 are provided and the inner main pump electrode 22, the auxiliary pump electrode 51, and the measurement electrode 44 are respectively disposed in these internal cavities. However, the structure of the sensor element 101 is not limited thereto. For example, the sensor element 101 may have a structure in which two internal cavities, the first internal cavity 20 and the second internal cavity 40 are provided, the inner main pump electrode 22 is disposed in the first internal cavity 20, and the auxiliary pump electrode 51 and the measurement electrode 44 are disposed in the second internal cavity 40. In this case, for example, a porous protective layer covering the measurement electrode 44 may be formed as a diffusion-rate limiting part between the auxiliary pump electrode 51 and the measurement electrode 44.

In the gas sensor 100 of the above embodiment, the outer pump electrode 23 has three functions as an outer main pump electrode in the main pump cell 21, an outer auxiliary pump electrode in the auxiliary pump cell 50, and an outer measurement electrode in the current measurement pump cell 41. However, the outer pump electrode 23 is not limited thereto. For example, the outer main pump electrode, the outer auxiliary pump electrode, and the outer measurement electrode may be formed as different electrodes. For example, any one or more of the outer main pump electrode, the outer auxiliary pump electrode, and the outer measurement electrode may be provided on the outer surface of the base part 102 separately from the outer pump electrode 23 so as to be in contact with a measurement-object gas. Alternatively, the reference electrode 42 may also serve as any one or more of the outer main pump electrode, the outer auxiliary pump electrode, and the outer measurement electrode.

As described above, according to the present invention, measurement can be performed while switching between the electromotive force measurement mode in which the measurement accuracy in low concentration is higher, and the current measurement mode in which the measurement accuracy in high concentration is higher, so that it is possible to accurately measure the target gas to be measured in a wide concentration range (for example, 10 to 5000 ppm) including the low concentration of the target gas to be measured. In the present invention, an upper limit of low concentration is intended to be less than 500 ppm. The target gas to be measured includes nitrogen atom-containing gases such as nitrogen oxide NOx and ammonia $NH_3$, as well as carbon dioxide $CO_2$, water $H_2O$ and the like, which generate a reducing gas by decomposition.

EXPLANATION OF REFERENCE SIGNS IN THE DRAWINGS

1: first substrate layer; 2: second substrate layer; 3: third substrate layer; 4: first solid electrolyte layer; 5: spacer layer; 6: second solid electrolyte layer; 10: gas inlet; 11: first diffusion-rate limiting part; 12: buffer space; 13: second diffusion-rate limiting part; 15: measurement-object gas flow part; 20: first internal cavity; 21: main pump cell; 22: inner main pump electrode; 22a: ceiling electrode portion (of the inner main pump electrode); 22b: bottom electrode portion (of the inner main pump electrode); 23: outer pump electrode; 24: variable power supply (of the main pump cell); 30: third diffusion-rate limiting part; 40: second internal cavity; 41: current measurement pump cell; 42: reference electrode; 43: reference gas introduction space; 44: measurement electrode; 46: variable power supply (of the current measurement pump cell); 47: switching unit; 48: air introduction layer; 50: auxiliary pump cell; 51: auxiliary pump electrode; 51a: ceiling electrode portion (of the auxiliary pump electrode); 51b: bottom electrode portion (of the auxiliary pump electrode); 52: variable power supply (of the auxiliary pump cell); 60: fourth diffusion-rate limiting part; 61: third internal cavity; 70: heater part; 71: heater electrode; 72: heater; 73: through hole; 74 heater insulating layer; 75: pressure relief vent; 76: heater lead; 77: heater power supply; 80: oxygen-partial-pressure detection sensor cell for main pump control; 81: oxygen-partial-pressure detection sensor cell for auxiliary pump control; 82: electromotive force detection sensor cell; 83: sensor cell; 90: control unit; 91: control part; 92: drive control part; 93: concentration calculating part; 94: measurement mode switching part; 100: gas sensor; 101: sensor element; and 102: base part.

What is claimed is:

1. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow part formed from one end part in a longitudinal direction of the base part;

an adjustment pump cell for adjusting an oxygen concentration in a measurement-object gas to a desired concentration, the adjustment pump cell including: an inner pump electrode disposed on an inner surface of the measurement-object gas flow part; and an outer pump electrode disposed at a position different from the measurement-object gas flow part on the base part and corresponding to the inner pump electrode;

a current measurement pump cell for detecting a target gas to be measured in the measurement-object gas as a current value, the current measurement pump cell including: an inner measurement electrode disposed at a position farther from the one end part in the longitudinal direction of the base part than the inner pump electrode on the inner surface of the measurement-object gas flow part; and an outer measurement electrode disposed at a position different from the measurement-object gas flow part on the base part and corresponding to the inner measurement electrode;

a reference electrode disposed inside the base part to be in contact with a reference gas; and an electromotive force detection sensor cell for detecting an electromotive force value between the inner measurement electrode and the reference electrode, the electromotive force detection sensor cell including the inner measurement electrode and the reference electrode, and the control unit comprises:

a switching unit for switching whether a current flows through the current measurement pump cell or not.

2. The gas sensor according to claim 1, wherein the control unit comprises:

a measurement mode switching part for switching between an electromotive force measurement mode in which a concentration of the target gas to be measured in the measurement-object gas is detected based on an electromotive force value in the electromotive force detection sensor cell, and a current measurement mode in which a concentration of the target gas to be measured in the measurement-object gas is detected based on a current value in the current measurement pump cell, and the measurement mode switching part switches the switching unit so that a current does not flow through the current measurement pump cell in case of switching to the electromotive force measurement mode, and switches the switching unit so that a current flows through the current measurement pump cell in case of switching to the current measurement mode.

3. The gas sensor according to claim 2, wherein the switching unit comprises a switch for switching whether a conduction in the current measurement pump cell is cut off or not.

4. The gas sensor according to claim 3, wherein the measurement mode switching part turns off the switch to cut off a conduction in the current measurement pump cell so that a current does not flow through the current measurement pump cell in case of switching to the electromotive force measurement mode, and turns on the switch to conduct the current measurement pump cell so that a current flows through the current measurement pump cell in case of switching to the current measurement mode.

5. The gas sensor according to claim 2, wherein the switching unit comprises a variable power supply for changing a voltage applied to the current measurement pump cell.

6. The gas sensor according to claim 5, wherein the measurement mode switching part sets a voltage in the variable power supply to zero not to apply a voltage in the current measurement pump cell so that a current does not flow through the current measurement pump cell in case of switching to the electromotive force measurement mode, and sets a voltage in the variable power supply to a predetermined value to apply the predetermined voltage in the current measurement pump cell so that a current flows through the current measurement pump cell in case of switching to the current measurement mode.

7. The gas sensor according to claim 2, wherein the measurement mode switching part switches to the electromotive force measurement mode when the measurement mode switching part determines that a concentration of the target gas to be measured detected in the current measurement mode is lower than a predetermined first concentration threshold value C1, and the measurement mode switching part switches to the current measurement mode when the measurement mode switching part determines that a concentration of the target gas to be measured detected in the electromotive force measurement mode is higher than a predetermined second concentration threshold value C2.

8. The gas sensor according to claim 7, wherein the first concentration threshold value C1 is lower than the second concentration threshold value C2.

9. The gas sensor according to claim 2, wherein in the current measurement mode, a current value in the current measurement pump cell is controlled so that an electromotive force value between the inner measurement electrode and the reference electrode in the electromotive force detection sensor cell is a predetermined value.

10. The gas sensor according to claim 1, wherein the reference electrode functions as the outer measurement electrode.

11. A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow part formed from one end part in a longitudinal direction of the base part;

an adjustment pump cell for adjusting an oxygen concentration in a measurement-object gas to a desired concentration, the adjustment pump cell including: an inner pump electrode disposed on an inner surface of the measurement-object gas flow part; and an outer pump electrode disposed at a position different from the measurement-object gas flow part on the base part and corresponding to the inner pump electrode;

a current measurement pump cell for detecting a target gas to be measured in the measurement-object gas as a current value, the current measurement pump cell including: an inner measurement electrode disposed at a position farther from the one end part in the longitudinal direction of the base part than the inner pump electrode on the inner surface of the measurement-object gas flow part; and an outer measurement electrode disposed at a position different from the measurement-object gas flow part on the base part and corresponding to the inner measurement electrode;

a reference electrode disposed inside the base part to be in contact with a reference gas; and an electromotive force detection sensor cell for detecting an electromotive force value between the inner measurement electrode and the reference electrode, the electromotive force detection sensor cell including the inner measurement electrode and the reference electrode, and the control unit comprises:

a switching unit for switching whether a current flows through the current measurement pump cell or not, and the control method comprising:

a concentration detecting step of performing an electromotive force measurement mode in which the adjustment pump cell is operated and the current measurement pump cell is not operated to detect a concentration of the target gas to be measured in the measurement-object gas based on an electromotive force value in the electromotive force detection sensor cell, or a current measurement mode in which the adjustment pump cell and the current measurement pump cell are operated to detect a concentration of the target gas to be measured in the measurement-object gas based on a current value in the current measurement pump cell, while switching between the electromotive force measurement mode and the current measurement mode by using the switching unit.

12. The control method according to claim 11, wherein, in the concentration detecting step, the switching unit is switched so that a current does not flow through the current measurement pump cell to switch to the electromotive force measurement mode when a concentration of the target gas to be measured detected in the current measurement mode is determined to be lower than a predetermined first concentration threshold value C1, and the switching unit is switched so that a current flows through the current measurement pump cell to switch to the current measurement mode when a concentration of the target gas to be measured detected in the electromotive force measurement mode is determined to be higher than a predetermined second concentration threshold value C2.

13. The control method according to claim 12, wherein the first concentration threshold value C1 is lower than the second concentration threshold value C2.

* * * * *